(12) United States Patent
Scheiflinger et al.

(10) Patent No.: US 9,617,523 B2
(45) Date of Patent: Apr. 11, 2017

(54) NUCLEIC ACIDS ENCODING VITAMIN K EXPOXIDE REDUCTASE SUBUNIT 1 AND VITAMIN K DEPENDENT PROTEIN EXPRESSION AND METHODS OF USING SAME

(75) Inventors: Friedrich Scheiflinger, Vienna (AT); Ernst Boehm, Vienna (AT)

(73) Assignees: Baxalta GmbH, Glattpark (Opfikon) (CH); Baxalta Incorporated, Bannockburn, IL (US)

( * ) Notice: Subject to any disclaimer, the term of this patent is extended or adjusted under 35 U.S.C. 154(b) by 0 days.

(21) Appl. No.: 11/342,299

(22) Filed: Jan. 27, 2006

(65) Prior Publication Data
US 2006/0194284 A1    Aug. 31, 2006

Related U.S. Application Data

(60) Provisional application No. 60/657,041, filed on Feb. 28, 2005.

(51) Int. Cl.
*A61K 38/00* (2006.01)
*C12N 9/04* (2006.01)

(52) U.S. Cl.
CPC ................................. *C12N 9/0006* (2013.01)

(58) Field of Classification Search
None
See application file for complete search history.

(56) References Cited

U.S. PATENT DOCUMENTS

| | | | |
|---|---|---|---|
| 7,482,141 B2 | 1/2009 | Stafford et al. | |
| 7,524,665 B2 | 4/2009 | Stafford et al. | |
| 7,645,602 B2 | 1/2010 | Stafford et al. | |
| 7,687,233 B2 | 3/2010 | Stafford et al. | |
| 2002/0102649 A1 | 8/2002 | Hillman et al. | |
| 2004/0058413 A1 | 3/2004 | Nicolaisen et al. | |
| 2007/0269866 A1* | 11/2007 | Stafford et al. | ............... 435/69.1 |
| 2013/0318640 A1 | 11/2013 | Oldenburg et al. | |

FOREIGN PATENT DOCUMENTS

| | | |
|---|---|---|
| EP | 1670947 A2 | 6/2006 |
| EP | 1 842 920 | 10/2007 |
| EP | 1861499 A1 | 12/2007 |
| WO | 90/03496 | 4/1990 |
| WO | 91/01372 | 2/1991 |
| WO | 92/01795 | 2/1992 |
| WO | 92/19636 | 11/1992 |
| WO | 02/29045 | 4/2002 |
| WO | WO 02/102994 A2 | 12/2002 |
| WO | 2005/030039 | 4/2005 |
| WO | 2005/040367 A1 | 5/2005 |
| WO | 2006/067116 | 6/2006 |
| WO | 2006/089613 | 8/2006 |
| WO | 2006/101474 | 9/2006 |
| WO | 2007/065173 | 6/2007 |
| WO | 2007/075976 | 7/2007 |

OTHER PUBLICATIONS

Seffernick et al. (J. Bacteriology, vol. 183, pp. 2405-2409, 2001).*
Wells, (Biochemistry, vol. 29, pp. 8509-8517, 1990).*
Berkner, K.L.; "The Vitamin K-Dependent Carboxylase"; *The Journal of Nutrition*; 130; pp. 1877-1880 (2000).
Derian, C.K., et al.; "Inhibitors of 2-Ketoglutarate-Dependent Dioxygenases Block Aspartyl β-Hydroxylation of Recombinant Human Factor IX in Several Mammalian Expression Systems"; *The Journal of Biological Chemistry*; 264:12; pp. 6615-6618 (1989).
Esmon, C.T., et al.; "The Functional Significance of Vitamin K Action"; *The Journal of Biological Chemistry*; 250:11; pp. 4095-4099 (1975).
Esmon, C.T., et al.; "A New Carboxylation Reaction"; *The Journal of Biological Chemistry*; 250:12; pp. 4744-4748 (1975).
European Pharmacopoeia 5.0; 2.7.10 Assay of Human Coagulation Factor VII; pp. 203-204 (2005).
Furie, B., et al.; "VitaminK-Dependent Biosynthesis of y-Carboxyglutamic Acid"; *Blood*; 93:6; pp. 1798-1808 (1999).
Furie, B., et al.; "The Molecular Basis of Blood Coagulation"; *Cell*; 53; pp. 505-508 (1988).
Hallgren, K.W., et al.; "Carboxylase Overexpression Effects Full Carboxylation but Poor Release and Secretion of Factor IX: Implications for the Release of Vitamin K-Dependent Proteins"; *Biochemistry*; 41:50; pp. 15045-15055 (2002).
Herlitschka, S.E., et al. "Overexpression of Human Prothrombin in Permanent Cell Lines Using a Dominant Selection/Amplification Fusion Marker"; *Protein Expression and Purification*; 8; pp. 358-364 (1996).
Himly, M., et al.; "Defective Vaccinia Virus as a Biologically Safe Tool for the Overproduction of Recombinant Human Secretory Proteins"; *Protein Expression and Purification*; 14; pp. 317-326 (1998).
International Search Report for PCT/EP2006/000734 (May 11, 2006).
Kaufman, R.J., et al.; "Expression, Purification, and Characterization of Recombinant y-Carboxylated Factor IX Synthesized in Chinese Hamster Ovary Cells"; *The Journal of Biological Chemistry*; 261:21; pp. 9622-9628 (1986).
Li, T., et al.; "Identification of the Gene for Vitamin K Epoxide Reductase"; *Nature*; 427; pp. 541-544.
Lin, P.J., et al.; "Binding of the Factor IX y-Carboxyglutamic Acid Domain to the Vitamin K-Dependent y-Glutamyl Carboxylase Active Site Induces an Allosteric Effect That May Ensure Processive Carboxylation and Regulate the Release of Carboxylated Product"; *The Journal of Biological Chemistry*;.279:8; pp. 6560-6566 (2004).
Malhotra, O.P., et al.; "The Kinetics of Activation of Normal and y-Carboxyglutamic Acid-Deficient Prothrombins"; *The Journal of Biological Chemistry*; 260:1; pp. 279-287 (1985).

(Continued)

*Primary Examiner* — Hope Robinson
(74) *Attorney, Agent, or Firm* — Wolf, Greenfield & Sacks, P.C.

(57) ABSTRACT

The present invention relates to a host organism containing recombinant nucleic acids coding for the vitamin K reductase complex subunit 1 (VKORC1) and recombinant nucleic acids coding for a vitamin K dependent (VKD) protein, wherein both the recombinant VKORC1 and the recombinant VKD protein are expressed in said host organism. Further, the present invention relates to a cell culture system comprising cells which contain said recombinant nucleic acids and to methods for improving the productivity of recombinant VKD protein expression in a host organism being cultured in suitable systems.

15 Claims, 11 Drawing Sheets

(56) References Cited

OTHER PUBLICATIONS

Mann, K.G., et al; "Cofactor Proteins in the Assembly and Expression of Blood Clotting Enzyme Complexes"; Ann. Rev. Biochem.; 57; pp. 915-956 (1988).
McGraw, R.A., et al.; "Evidence for a Prevalent Dimorphism in the Activation Peptide of Human Coagulation Factor IX". *Proc. Natl. Acad. Sci. USA*; 82; pp. 2847-2851 (1985).
Moor, E., et al.; "Coagulation Factor VII Mass and Activity in Young Men with Myocardial Infarction at a Young Age"; *Arteriosclerosis, Thrombosis and Vascular Biology*; 15:5; pp. 655-664 (1995).
Morrissey, J.H., et al.; "Quantitation of Activated Factor VII Levels in Plasma Using a Tissue Factor Mutant Selectively Deficient in Promoting Factor VII Activation"; *Blood*; 81:3; pp. 734-744 (1993).
Mountford, P.S., et al.; "Internal Ribosome Entry Sites and Dicistronic RNAs in Mammalian Transgenesis"; *Trends in Genetics*; 11:5; pp. 179-184 (1995).
Nelsestuen, G.L., et al.; "Role of γ-Carboxyglutamic Acid"; *The Journal of Biological Chemistry*; 251:22; pp. 6886-8693 (1976).
Nelsestuen, G.L., et al.; "The Mode of Action of Vitamin K"; *The Journal of Biological Chemistry*; 219:19; pp. 6347-6350 (1974).
Rehemtulla, A., et al.; "In vitro and in vivo Functional Characterization of Bovine Vitamin K-Dependent γ-Carboxylase Expressed in Chinese Hamster Ovary Cells"; *Proc. Natl. Acad. Sci. USA*; 90; pp. 4611-4615 (1993).
Rost, S., et al.; "Mutations in VKORC1 Cause Warfarin Resistance and Multiple Coagulation Factor Deficiency Type 2"; *Nature*; 427; pp. 537-541 (2004).
Scahill, S.J., et al; "Expression and Characterization of the Product of a Human Immune Interferon cDNA Gene in Chinese Hamster Ovary Cells"; *Proc. Natl. Acad. Sci. USA*; 80; pp. 4654-4658 (1983).
Stenflo, J., et al.; "Vitamin K-Dependent Formation of γ-Carboxyglutamic Acid"; *Ann. Rev. Biochem.*; 46; pp. 157-172 (1977).
Sun, Y-M., et al.; "Vitamin K Epoxide Reductase Significantly Improves Carboxylation in a Cell Line Overexpressing Factor X"; *Blood*; 106:12; pp. 3811-3815 (2005).
Suttie, J.W.; "Mechanism of Action of Vitamin K: Synthesis of γ-Carboxyglutamic Acid"; *CRC Critical Reviews in Biochemistry*; pp. 191-223 (1980).
Vermeer, C., et al.; "Vitamin K-Dependent Carboxylase"; *Haematologia*; 18:2; pp. 71-97 (1985).
Wajih, N., et al.; "Engineering of a Recombinant Vitamin K-Dependent γ-Carboxylation System with Enhanced γ-Carboxylglutamic Acid Forming Capacity"; *The Journal of Biological Chemistry*; 280:11; pp. 10540-10547 (2005).
Wajih, N., et al.; "Increased Production of Functional Recombinant Human Clotting Factor IX by Baby Hamster Kidney Cells Engineered to Overexpress VKORC1, the Vitamin K 2,3-Epoxide-Reducing Enzyme of the Vitamin K Cycle"; *The Journal of Biological Chemistry*; 280:36; pp. 31603-31607 (2005).
Wallin, R., et al.; "Vitamin K 2,3-Epoxide Reductase and the Vitamin K-Dependent γ-Carboxylation System"; *Thrombosis Research*; 108:4; pp. 221-226 (2003).
Ware, J., et al.; "Factor IX San Dimas"; *The Journal of Biological Chemistry*; 264:19; pp. 11401-11406.
Wasley, L.C., et al.; "PACE/Furin Can Process the Vitamin K-Dependent Pro-Factor IX Precursor Within the Secretory Pathway"; *The Journal of Biological Chemistry*; 268:12; pp. 8458-8465 (1993).
Zhang, L., et al.; "Role of Individual γ-Carboxyglutamic Acid Residues of Activated Human Protein C in Defining its In Vitro Anticoagulant Activity"; *Blood*; 80:4; pp. 942-952 (1992).
Zwaal, R.F.A., et al.; "Lipid-Protein Interactions in Blood Coagulation"; *Biochimica et Biophysica Acta*, 1376; pp. 433-453 (1998).
Extended European Search Report in 10010933.9, dated Jan. 31, 2011.
Office Action in IL 176539, dated Sep. 21, 2010.
Vermeer, Biochem J., 266(3):625-636 (1990).
Office Action in JP 2007-557348, dated May 10, 2012.
Notice of Opposition against EP Patent 1 853 700, dated Jul. 23, 2013, filed by Marie Christina Gates of Tomkins & Co. Intellectual Property, 13 pages.
Wallin, Reider, et al., "Vitamin K-dependent Carboxylation and Vitamin K Metabolism in Liver: Effects of Warfarin", J. Clin. Invest., Nov. 1985, vol. 76, pp. 1879-1884.
Notice of Preliminary Rejection in KR 10-2007-7022018 dated Aug. 27, 2012.
GenBank Accession No. AAA88040: coagulation factor VII [*Homo sapiens*] (Feb. 13, 1996).
Kojima et al., "The function of GADD34 is a recovery from a shutoff of protein synthesis induced by ER stress: elucidation by GADD34-deficient mice," FASEB J., 17(11):1573-1575 (2003).
Office Action in EP 10010933.9, dated Nov. 15, 2011.
Office Action in CN 200680004712.4, dated Jan. 25, 2011.
Wajih et al., J. Biol. Chem., 280(11):10540-10547 (2005).
Office Action in IL 184696, dated Sep. 21, 2010.
Rehemtulla et al., PNAS, 90:4611-4615 (1993).
Office action in EP 1001933.9, dated Nov. 15, 2011.
Decision of Re-examination in China issued for Chinese Patent Application No. 200680004712.4, dated Jul. 31, 2013, 12 pages.
Berkner KL, Runge KW. The physiology of vitamin K nutriture and vitamin K-dependent protein function in atherosclerosis. J Thromb Haemost. Dec. 2004;2(12):2118-32.
McClure DB, Walls JD, Grinnell BW. Post-translational processing events in the secretion pathway of human protein C, a complex vitamin K-dependent antithrombotic factor. J Biol Chem. Sep. 25, 1992;267(27):19710-7.
Nishimoto SK, Price PA. Secretion of the vitamin K-dependent protein of bone by rat osteosarcoma cells. Evidence for an intracellular precursor. J Biol Chem. Jul. 25, 1980;255(14):6579-83.
Response filed in Opposition against EP Patent 1 853 700, dated Apr. 2, 2015, filed by J. W. G. Jappy of Gill Jennings & Every LLP, 27 pages.
European Office Action issued by the European Patent Office for Application No. 10010933.9 dated Oct. 27, 2014(4 pages).
Summons to attend oral proceedings pursuant to Rule 115(1) EPC issued by the European Patent Office for Application No. 06706455.0 dated Oct. 31, 2014 (8 pages).
Wallin, R. et al "Vitamin K 2,3-epoxide reductase and the vitamin K-dependent γ-carboxylation system," Thrombosis Research, vol. 108, Issue 4, pp. 221-226 (2003).
GenBank Accession No. AY423044.1. *Homo sapiens* vitamin K epoxide reductase complex subunit 1 (VKORC1) mRNA, complete cds. Retrieved Apr. 17, 2015. 3 pages. (http://www.ncbi.nlm.nih.gov/nuccore/AY423044).
GenBank Accession No. AY423047.1. Rattus norvegicus vitamin K epoxide reductase complex subunit 1 (Vkorc1) mRNA, complete cds. Retrieved Apr. 17, 2015. 3 pages. (http://www.ncbi.nlm.nih.gov/nuccore/AY423047).
GenBank Accession No. NM_203335.2. Rattus norvegicus vitamin K epoxide reductase complex, subunit (Vkorc1), mRNA. Retrieved Sep. 25, 2015. 3 pages. (http://www.ncbi.nlm.nih.gov/nuccore/NM_203335.2).
[No Author Listed], definition for term "could"; MacmillanDictionary.com. Web. Sep. 25, 2015. http://www.macmillandictionary.com/dictionary/british/could.
[No Author Listed], definition for term "likely"; MacmillanDictionary.com. Web. Sep. 25, 2015. http://www.macmillandictionary.com/dictionary/british/likely_1.
U.S. Appl. No. 14/746,121, filed Jun. 22, 2015.

\* cited by examiner

A

B

NUCLEIC ACIDS ENCODING VITAMIN K EXPOXIDE REDUCTASE SUBUNIT 1 AND VITAMIN K DEPENDENT PROTEIN EXPRESSION AND METHODS OF USING SAME

CROSS-REFERENCES TO RELATED APPLICATIONS

This application claims the benefit of U.S. Patent Application No. 60/657,041, filed Feb. 28, 2005, the disclosure of which is hereby incorporated by reference in its entirety for all purposes.

FIELD OF THE INVENTION

The present invention relates to a host organism containing recombinant nucleic acids coding for the vitamin K reductase complex subunit 1 (VKORC1) and recombinant nucleic acids coding for a vitamin K dependent (VKD) protein, wherein both the recombinant VKORC1 and the recombinant VKD protein are expressed in said host organism. Further, the present invention relates to a cell culture system comprising cells which contain said recombinant nucleic acids and to methods for improving the productivity of recombinant VKD protein expression in a host organism being cultured in suitable systems.

BACKGROUND OF THE INVENTION

The vitamin K epoxide reductase complex (VKORC) recycles the reduced form of vitamin K which is an essential cofactor for post-translational γ-carboxylation of vitamin K dependent (VKD) proteins (Nelsestuen et al. (1974) The mode of action of vitamin K. Identification of gamma-carboxyglutamic acid as a component of prothrombin. *J. Biol. Chem.*, 249, 6347-6350). The VKORC1 gene was identified recently, and is described in detail in Rost et al. (2004) Mutations in VKORC1 cause warfarin resistance and multiple coagulation factor deficiency type 2. *Nature*, 427, 537-541).

VKD proteins contain γ-carboxylated glutamate (gla) residues giving them specific biochemical and physiological properties like Ca-dependent binding to negatively charged phospholipid membranes in the case of blood clotting factors (Mann et al. (1988) Cofactor proteins in the assembly and expression of bloodclotting enzyme complexes. *Annu. Rev. Biochem.*, 57, 915-956). VKD proteins include procoagulant factors II, VII, IX and X, and anticoagulant proteins C, S and Z. Although restricted to one single known enzymatic reaction, γ-carboxylase activity is found in all mammalian tissues (Vermeer and de Boer-van den Berg MA (1985) Vitamin K-dependent carboxylase. *Haematologia (Budap.)*, 18, 71-97). The γ-carboxylase catalyzes a carboxylation reaction using reduced vitamin K as cofactor.

Vitamin K dependent (VKD) gamma carboxylation of glutamic acid residues is a post-translational protein modification required for the generation of biologically active VKD proteins playing roles in hemostasis, growth control, calcium homeostasis, and signal transduction (Furie et al. (1999) Vitamin K-dependent biosynthesis of gamma-carboxyglutamic acid. *Blood*, 93, 1798-1808; Berkner, K. L. (2000) The vitamin K-dependent carboxylase. *J. Nutr.*, 130, 1877-1880). Several glutamic acid residues in the N-terminal Gla-domain of these proteins are modified by carboxylation to enable calcium-dependent phospholipid membrane interactions (Stenflo and Suttie (1977) Vitamin K-dependent formation of gamma-carboxyglutamic acid. *Annu. Rev. Biochem.*, 46, 157-172; Suttie (1980) Mechanism of action of vitamin K: synthesis of gamma-carboxyglutamic acid *CRC Crit Rev. Biochem.*, 8, 191-223). These multiple gamma-glutamate (Gla) residues allow the Gla domain to undergo conformational changes which are required for the activity of VKD proteins in combination with binding to phospholipid membrane surfaces (Nelsestuen et al. (1976) Role of gamma-carboxyglutamic acid. Cation specificity of prothrombin and factor X-phospholipid binding. *J. Biol. Chem.*, 251, 6886-6893; Zwaal et al. (1998) Lipid-protein interactions in Blood coagulation. *Biochim. Biophys. Acta*, 1376, 433-453).

The VKD blood coagulation proteins require full or nearly full carboxylation to bind to membrane surfaces in the presence of calcium ions (Furie and Furie (1988) The molecular basis of blood coagulation. *Cell*, 53, 505-518). If vitamin K antagonists inhibit gamma carboxylation, thus undercarboxylated VKD proteins cannot form the calcium dependent structure which results in low affinity to phospholipids membranes and less activity (Esmon et al. (1975a) A new carboxylation reaction. The vitamin K-dependent incorporation of H-14-CO3-into prothrombin. *J. Biol. Chem.*, 250, 4744-4748; Esmon et al. (1975b) The functional significance of vitamin K action. Difference in phospholipid binding between normal and abnormal prothrombin. *J. Biol. Chem.*, 250, 4095-4099; Malhotra, O. P., Nesheim, M. E., & Mann, K. G. (1985) The kinetics of activation of normal and gamma-carboxyglutamic acid-deficient prothrombins. *J. Biol. Chem.*, 260, 279-287). For example, contributions to overall protein activity losses could be assigned to the absence of each of the 10 Gla-residues of the VKD protein activated human protein C (Zhang et al. (1992) Role of individual gamma-carboxyglutamic acid residues of activated human protein C in defining its in vitro anticoagulant activity. *Blood*, 80, 942-952). Missing procoagulant activity of undercarboxylated factor IX mutants found in hemophilia B patients can be assigned to impaired calcium-induced conformational changes and loss in the ability to bind phospholipid vesicles (Ware et al. (1989) Factor IX San Dimas. Substitution of glutamine for Arg-4 in the propeptide leads to incomplete gamma-carboxylation and altered phospholipid binding properties. *J. Biol. Chem.*, 264, 11401-11406).

In case of recombinant factor IX, it has been shown that expression of functional factor IX in Chinese hamster ovary cells is limited by the fact that carboxylation ability is saturated at higher production levels (Kaufinan et al. (1986) Expression, purification, and characterization of recombinant gamma-carboxylated factor IX synthesized in Chinese hamster ovary cells. *J. Biol. Chem.*, 261, 9622-9628; Derian et al. (1989) Inhibitors of 2-ketoglutarate-dependent dioxygenases block aspartyl beta-hydroxylation of recombinant human factor IX in several mammalian expression systems. *J. Biol. Chem.*, 264, 6615-6618).

Recombinant over-expression of γ-carboxylated proteins was shown in case of human factor IX to lead to a limitation of propeptide cleavage and γ-carboxylation at higher secretion rates, thus yielding proteins which are only partially occupied with gla residues also when vitamin K is available in the culture medium in surplus. This leads to the secretion of variants of VKD recombinant proteins with reduced activities. Addition of vitamin K to the medium did not improve factor IX activity at high expression levels. The requirement of vitamin K present in the cell culture medium to elicit active factor IX was shown to reach saturation at 5 µg/ml. Below this level, the secreted amount of active factor IX from Chinese hamster ovary (CHO) cells was dependent on vitamin K concentration (Kaufinan et al. (1986) Expression, purification, and characterization of recombinant gamma-carboxylated factor IX synthesized in Chinese hamster ovary cells. *J. Biol. Chem.*, 261, 9622-9628).

Up to now cell lines with low expression levels have to be chosen for production in order to overcome these limitations of cellular capacity to modify VKD proteins post-translationally. Co-expression of Furin, the propeptide cleaving enzyme, leads to complete cleavage of this propeptide (Wasley et al. (1993) PACE/furin can process the vitamin K-dependent pro-factor IX precursor within the secretory pathway. *J. Biol. Chem.*, 268, 8458-8465), but is not involved in γ-carboxylation improvement. Another approach, the overexpressing of γ-carboxylase, has not led to improved protein secretion in case of factor IX (Rehemtulla et al. (1993) In vitro and in vivo functional characterization of bovine vitamin K-dependent gamma-carboxylase expressed in Chinese hamster ovary cells. *Proc. Natl. Acad. Sci. U.S.A*, 90, 4611-4615). Factor IX molecules, which are bound to the carboxylase during the carboxylation reaction are not released effectively. It was concluded that the supply of reduced vitamin K form at the site of γ-carboxylation is the limiting step of this reaction (Hallgren et al. (2002) Carboxylase overexpression effects full carboxylation but poor release and secretion of factor IX: implications for the release of vitamin K-dependent proteins. *Biochemistry*, 41, 15045-15055).

Therefore, a strong need exists for stabilizing the expression, particularly the recombinant expression of VKD proteins in host organisms yielding in improved secretion rates and/or activities of the expressed VKD proteins.

Thus, it is an object of the present invention to provide new systems and methods for improving the productivity of (particularly recombinant) VKD protein expression via co-expression of VKORC1.

BRIEF SUMMARY OF THE INVENTION

The present invention relates to a host organism containing a recombinant nucleic acid coding for a vitamin K reductase complex subunit 1 (VKORC1) or a functionally active derivative thereof, and a recombinant nucleic acid coding for a vitamin K dependent (VKD) protein or a functionally active derivative thereof, wherein both the recombinant VKORC1 and the recombinant VKD protein are expressed in said host organism.

Further, the present invention relates to a cell culture system comprising cells which contain a recombinant nucleic acid coding for VKORC1 or a functionally active derivative thereof and a recombinant nucleic acid coding for a VKD protein or a functionally active derivative thereof, wherein both the recombinant VKORC1 and the recombinant VKD protein are expressed in said cells, to methods for improving the productivity of recombinant VKD protein expression or of a functionally active derivative thereof in a host organism by recombinantly co-expressing VKORC1, and to the use of a recombinant expression of VKORC1 in a host organism or cell culture system for improving the productivity of recombinant VKD expression.

BRIEF DESCRIPTION OF THE DRAWINGS

FIG. 5A shows productivity values based on ELISA measurements. FIG. 5B shows productivity values based on clotting activity measurements. FIG. 5C shows specific FVII activity calculation based on FVII-clotting units per μg as determined by ELISA.

FIG. 11A shows results from CHO-derived cell clones and FIG. 11B shows results from HEK293-derived cell clones.

DETAILED DESCRIPTION OF THE INVENTION

Figure 1:
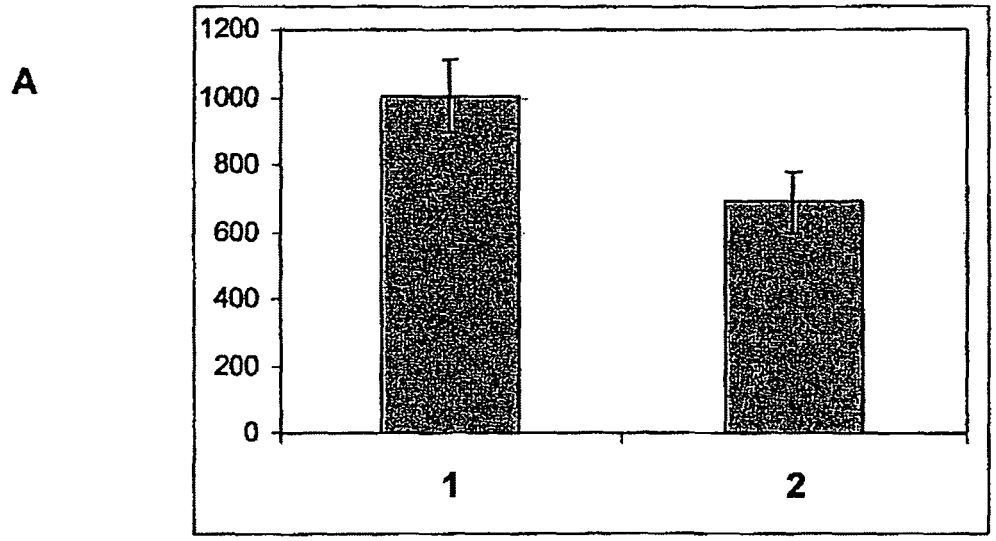
FIG. 1 shows the concentrations of rFIX in ng/ml (vertical axis) calculated on the basis of ELISA values (FIG. 1A) and the specific activities of rFIX calculated on the basis of clotting activity (APTT) values in mU/ml (vertical axis) (FIG. 1B) after transient transfections of a CHO-derived rFIX producing cell line with rVKORC1 (1) or an empty vector (2). Serum-free cell culture supernatants were collected after 24 hours.
Figure 1:
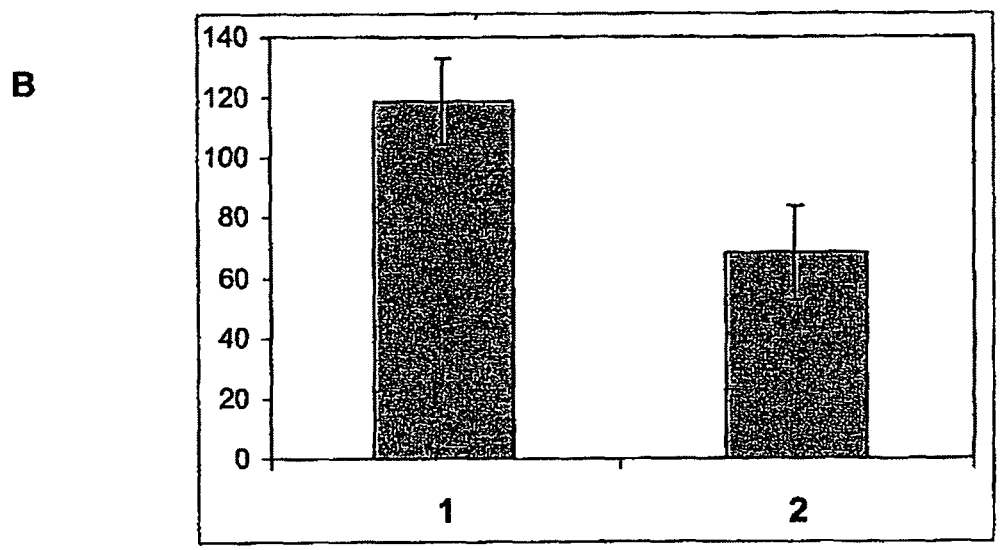
Figure 2:
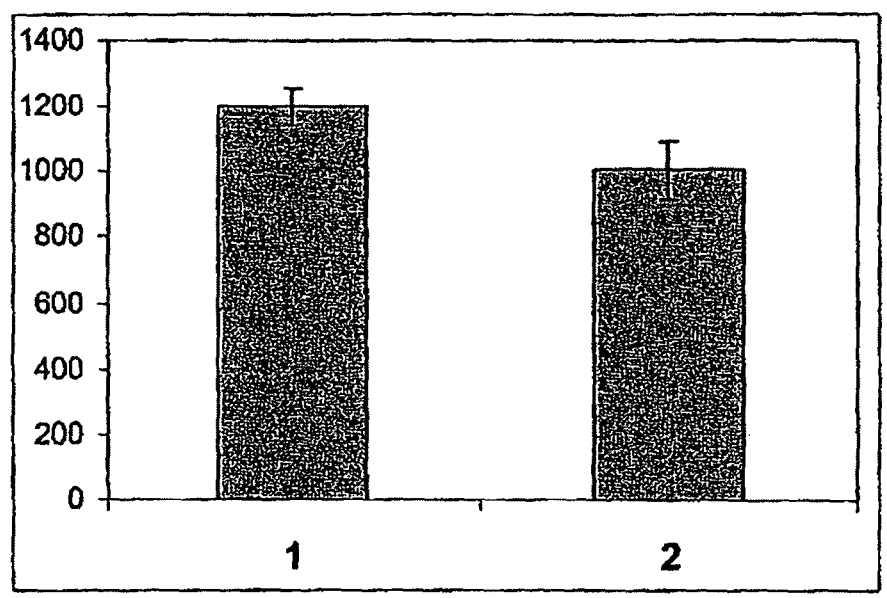
FIG. 2 shows the specific productivities of rFIX in ng rFIX/$10^6$ cells/day (vertical axis) calculated on the basis of ELISA values (FIG. 2A) and the specific activities of rFIX calculated on the basis of clotting activity (APTT) values in mU rFIX/$10^6$ cells/day (vertical axis) (FIG. 2B) after transient transfections of a CHO-derived rFIX producing cell line with rVKORC1 (1) or an empty vector (2). Serum-free cell culture supernatants were collected after 24 hours.
Figure 2:
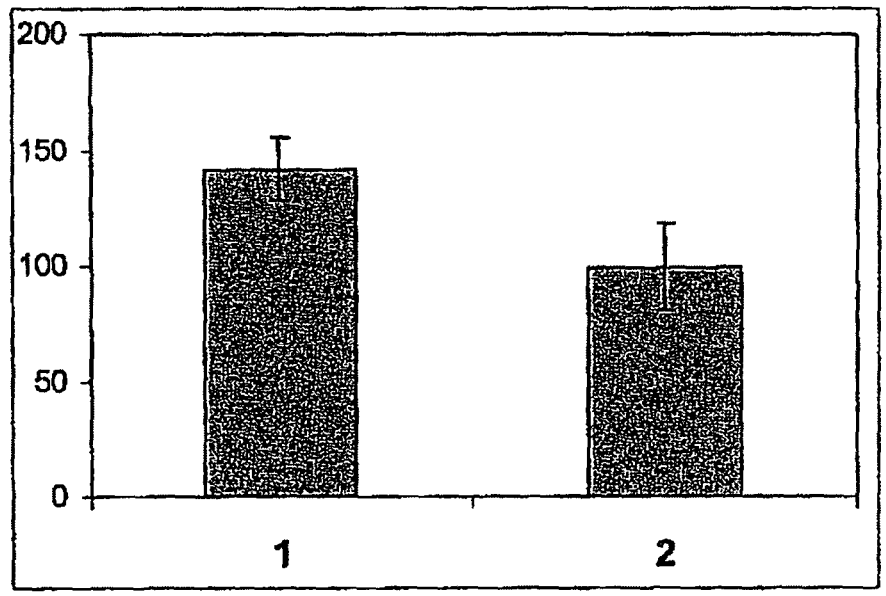

One aspect of the present invention relates to a host organism containing a recombinant nucleic acid coding for a vitamin K reductase complex subunit 1 (VKORC1) or a functionally active derivative thereof, and a recombinant nucleic acid coding for a vitamin K dependent (VKD) protein or a functionally active derivative thereof, wherein both the recombinant VKORC1 and the recombinant VKD protein are expressed in said host organism.

The term "functionally active derivative" as used herein means any polypeptide with substantially the same biological function as VKORC1 and VKD proteins respectively. The polypeptide sequences of the functionally active derivatives may contain deletions, additions and/or substitution of amino acids whose absence, presence and/or substitution, respectively, do not have any substantial negative impact on the activity of the polypeptide, e.g. amino acids which are located in a part of the polypeptide sequence that does not contribute to the biological activity of the protein. Minor deletions, additions and/or substitutions of amino acids of the respective polypeptide sequences which are not altering the biological activity of said polypeptide are also included in the present application as functionally active derivatives.

In the following the expressions "(recombinant) VKORC1 or a functionally active derivative thereof" and "(recombinant) VKD protein or a functionally active derivative thereof" will also be designated as "(r)VKORC1" and "(r)VKD protein", respectively.

The recombinant nucleic acids of the present invention may be obtained by any method known in the art for the production of recombinant nucleic acids, e.g. via recombinant DNA-technology, reverse transcription of RNA and/or amplification of DNA, or via bacterial reproduction.

The host organism of the present invention may be derived from any host organism, including recombinant host organisms, which is capable of expressing a biologically active rVKORC1 and a biologically active rVKD protein. In particular, the host organism of the present invention may be a eukaryotic host organism, including multicellular organisms, characterized by producing a pharmacologically active rVKD protein.

In one embodiment of the present invention the host organism is a mammalian cell, for example a cell derived from a mammalian cell line selected from the group consisting of CHO cells, HEK293 cells, NS0 cells, Sp20 cells, Perc.6 cells, SkHep cells, HepG2 cells, BHK cells, HeLa cells, Vero cells, and COS cells. In specific examples of the present invention the host organism is a cell derived from CHO cells or HEK293 cells.

In one embodiment of the present invention either the nucleic acid coding for rVKORC1 or the nucleic acid coding for the rVKD protein or both contained in the host organism of the present invention are expressed via an expression mode selected from the group consisting of induced, transient, and permanent expression. Any expression system known in the art or commercially available can be employed for the expression of the recombinant nucleic acids coding for VKORC1 and/or VKD protein, including the use of regulatory systems such as suitable, preferably controllable promoters, enhancers etc.

In a preferred embodiment of the host organism of the present invention either the recombinant nucleic acid coding for VKORC1 or the recombinant nucleic acid coding for a VKD protein or both are stably integrated into the genetic material of the host organism of the present invention.

The host organism of the present invention can be used for the improved expression of rVKD proteins such as blood factors or functionally active derivatives thereof, preferably human procoagulant or anticoagulant blood factors or functionally active derivatives thereof. In a preferred embodiment of the present invention the rVKD protein is a pharmacologically acceptable human procoagulant blood factor which can be used in the treatment of bleeding disorders.

As an example of the present invention the rVKD protein is a procoagulant blood factor, including factor II, factor VII, factor IX, preferably human factor IX, and factor X, or an anticoagulant blood factor, including protein C, protein S and protein Z.

According to the present invention the host organism contains a recombinant nucleic acid coding for VKORC1 and a recombinant nucleic acid coding for a VKD protein, wherein both the rVKORC1 and the rVKD protein are expressed in said host organism and wherein the productivity of recombinant VKD protein expression is substantially improved.

The term "wherein the productivity of recombinant VKD protein expression is substantially improved" as used herein means that the amount, secretion rate, activity, and/or stability of a recombinantly expressed VKD protein or a functionally active derivative thereof is substantially increased when compared to the expression of the rVKD protein in a host organism which does not co-express rVKORC1.

The improvement of the productivity of recombinant VKD protein expression can be determined by any method known in the art including the isolation, e.g. from a culture medium or by harvesting the host organism, and analysis, e.g. via electrophoresis, chromatography, or immunoadsorption, of the expressed proteins. In a preferred embodiment of the present invention the expression of the rVKD proteins is detected via any known enzyme immuno assay such as an enzyme-linked immuno-sorbent assay (ELISA). Alternatively, the integrity and activity of the rVKD protein may be assessed by measuring the activated partial thromboplastin time (APTT).

Another aspect of the present invention relates to a cell culture system comprising cells which contain a recombinant nucleic acid coding for VKORC1 and a recombinant nucleic acid coding for a VKD protein, wherein both the rVKORC1 and the rVKD protein are expressed in said cells.

The cell culture system of the present invention may comprise any cell culture system which contains cells capable of expressing a biologically active rVKORC1 and a biologically active rVKD protein. Examples of suitable cells are listed above. In a preferred embodiment the cell culture system of the present invention is an eukaryotic cell system characterized by producing one or more pharmacologically active rVKD proteins.

In one embodiment of the present invention the cell culture system of the present invention comprises a host organism as defined above.

There is no particular limitation to the media, reagents and conditions used for culturing the cells in the cell culture system of the present invention including culturing the cells in a continuous or batchwise manner. In one embodiment of the present invention the cells are cultured under serum-free or serum- and protein-free conditions. In a further embodiment of the present invention conditions are employed under which cells which contain a recombinant nucleic acid coding for VKORC1 or a VKD protein are selectively proliferated, e.g. by using a selective medium.

The desired rVKD protein which has been expressed by the cells of the selected host organism and which, dependent on the transfection/vector-system used, is contained in the cells or secreted into the medium for culturing cells, can be isolated/recovered from the cell culture system using methods known in the art.

It is a further aspect of the present invention to provide a method for improving the specific activity of recombinant VKD protein expressed in a host organism comprising the steps of:
 (a) providing a host organism;
 (b) inserting a recombinant nucleic acid coding for a VKD protein or a functionally active derivative thereof into the host organism of step (a);
 (c) inserting a recombinant nucleic acid coding for VKORC1 into the host organism of step (a); and
 (d) expressing the recombinant nucleic acids of steps (b) and (c).

In one embodiment of the present invention the recombinant nucleic acids coding for VKORC1 or a VKD protein are inserted into the host organism simultaneously via co-transfection. Alternatively, said recombinant nucleic acids are inserted into the host organism sequentially via subsequent transfections.

The recombinant nucleic acids used according to the present invention may be contained in any form and system suitable for the transfection into a host organism including plasmids and viral vectors. The recombinant nucleic acids coding for VKORC1 and a VKD protein, respectively may be both present in one vector molecule or each in one vector molecule, wherein the two different vector molecules may be the same or different. The transfection of the recombinant nucleic acids depends on the transfection system used and may be carried out by any method known in the art or commercially available for transfecting a host organism like for example a eukaryotic cell including electroporation, precipitation, or microinjection.

It is another aspect of the present invention to provide a method for improving the productivity of recombinant VKD protein expression in a host organism comprising the steps of:
 (a) providing a host organism having a recombinant nucleic acid coding for a VKD protein integrated into its genetic material, preferably its genome;
 (b) inserting a recombinant nucleic acid coding for VKORC1 into the host organism of step (a); and
 (c) expressing the nucleic acids of steps (a) and (b).

In a preferred embodiment of the present invention the recombinant nucleic acid coding for a VKD protein is stably expressed.

It is a further aspect of the present invention to provide a method for improving the productivity of recombinant VKD protein expression in a host organism comprising the steps of:
 (a) providing a host organism having a recombinant nucleic acid coding for VKORC1 integrated into its genome;
 (b) inserting a recombinant nucleic acid coding for a VKD protein into the host organism of step (a); and
 (c) expressing the nucleic acids of steps (a) and (b).

In a preferred embodiment of the present invention the recombinant nucleic acid coding for VKORC1 is stably expressed.

According to the present invention the above-defined host-organism or the above-defined cell culture system can be used for improving surprisingly the productivity of recombinant VKD protein expression by co-expression of rVKORC1.

It is further an object of the present invention to provide a rVKD protein obtainable by inserting a recombinant nucleic acid coding for VKORC1 and a recombinant nucleic acid coding for said rVKD protein, expressing said nucleic acids, and recovering said rVKD protein.

The present invention will be further illustrated in the following examples without any limitation thereto.

EXAMPLES

Example 1

Transient Transfection and Co-Expression of rVKORC1 in rFIX-Producing HEK293- and CHO-Derived Cell Lines The expression of recombinant factor IX (rFIX) is achieved by introducing expression plasmids containing the human factor IX (FIX) encoding DNA sequence under the control of a strong viral promoter into mammalian host cell lines by an appropriate transfection method resulting in cells having the introduced sequences stably integrated into their genomes. The plasmids also confer resistance to a selectable marker drug by delivering the adequate resistance gene(s). In the case of CHO cells, which are able to grow only in presence of nucleotide precursors in the medium because of an enzyme defect of the nucleotide de-novo synthesis pathway, the expression of this enzyme, dihydrofolate-reductase (DHFR), is required. This enables co-amplification of the FIX gene by gradually increasing the concentration of methotrexate (MTX), which leads to an increase of copy numbers of both genes, encoding DHFR and rFIX, within the cell's genome. For that purpose, CHO derived cell clones have to be grown also in selective medium lacking nucleotides and nucleotide precursors.

For the identification of human rFIX producing cells, after transfection and addition of the selective drug(s) to the medium, the cell suspension is diluted to enable isolation of single-cell derived clones. After isolation, these cell clones are cultivated to confluency to enable measurement of rFIX content of the cell culture supernatant by enzyme-linked immuno-sorbent assay (ELISA) technique. For that purpose, the cells have to be grown in the absence of any growth promoting fetal bovine serum or components thereof to ensure identification of by the cells secreted rFIX. To ensure a fully functional rFIX protein, vitamin K is added. The supernatant is harvested after 24 hours and analyzed by rFIX-specific ELISA technique. In addition, the protein's integrity and activity is assessed by measuring activated partial thromboplastin time (APTT).

Co-expression of rVKORC1 is accomplished by transient expression techniques using cell lines, which are already selected for rFIX expression. An expression plasmid comprising rVKORC1 cDNA is transfected into these cells without further clone selection. The supernatants are collected from the whole transfected cell pools, and rFIX content and activity are compared to negative controls and normalized for specific rFIX secretion rates to assess effects of rVKORC1 activity.

Materials and Methods:
Expression Vectors

The expression vectors are cloned according to standard cloning techniques. Briefly, pSV-DHFR is generated by inserting the PstI 1.5 kbp fragment of vector pAdD26SV (A)-3 (Scahill et al. (1983) Expression and characterization of the product of a human immune interferon cDNA gene in Chinese hamster ovary cells. *Proc. Natl. Acad. Sci. U.S.A*, 80, 4654-4658; vector is a gift by Dr. Hauser, GBF Germany) containing murine DHFR into a pSVβ vector (Clontech, Palo Alto, Calif.) providing the SV40 enhancer, early promoter and intron, where the β-galactosidase gene has been removed by NotI digestion, and a polylinker has been inserted. This vector has also been used to generate phact containing the human actin promoter and intron by exchanging the EcoR/HindIII fragment with the EcoR/HindIII fragment of ph□APr-1-βgal, which is also a gift by Dr. Hauser. phact-FIX containing wild-type human FIX cDNA with the ala148 polymorphism (McGraw et al. (1985) Evidence for a prevalent dimorphism in the activation peptide of human coagulation factor IX. *Proc. Natl. Acad. Sci. U.S.A*, 82, 2847-2851) is generated by EcoRI digestion of pFIX-bluescript, which has been generated by inserting human FIX from a randomly primed human liver cDNA library into pBluescript (Stratagene, La Jolla, Calif.), and inserting the resulting fragment into phact partially digested with EcoRI.

The vector pCMV-FIX-neo is generated by inserting the EcoRI fragment of vector pFIX-bluescript into pCMV□ (Clontech), where the β-gal cDNA has been removed. Within this vector, the codon for ala is exchanged to thr by site-specific mutagenesis via PCR, changing the naturally occurring polymorphism of ala148 to thr148. The PCR product is re-inserted into the same vector again. The EcoRI fragment of this vector is cloned into pcDNA3.1 (Invitrogen, Carlsbad, Calif.) to yield pCMV-FIX-neo.

The vector pCMV-VKORC1-EDHpro is generated by using the vector pCEP4-VKORC1 (kindly provided by Prof. Oldenburg, for description see Rost et al., 2004) as a template for PCR. The PCR product containing the rVKORC1 cDNA is cloned into the pCMV-EDHpro vector (Herlitschka et al. (1996) Overexpression of human prothrombin in permanent cell lines using a dominant selection/amplification fusion marker. *Protein Expr. Purif,* 8, 358-364).

Cell Culture and Transfections

CHO DUKX/DXB11 cells are obtained from Columbia University (New York, N.Y.) and are cultivated in DMEM/Ham's F12 (1:1) mix (Invitrogen) supplemented with 5% fetal bovine serum (PAA, Linz, Austria), desoxy-adenosine, adenosine and thymidine (all from Sigma, St. Louis, Mo.) and L-Glutamine (Invitrogen) and penicillin/streptomycin (Invitrogen). HEK293 cells (ATCC No. CRL-1573) are cultivated in DMEM/Ham's F12 (1:1) mix supplemented with 5% fetal bovine serum and L-Glutamine and penicillin/streptomycin. For stable transfections, a calcium-phosphate co-precipitation method is used. CHOrFIX cells are generated by co-transfection with the linearized plasmids phact-FIX and pSV-DHFR and by selection in DMEM/Ham's F12 (1:1) mix without hypoxanthine, glycine, and thymidine (Invitrogen) supplemented with 5% dialyzed FBS (PAA). For gene amplification, MTX (Ebewe, Unterach, Austria) is added in stepwise increased concentrations beginning with 10 nM up to 200 nM. HEK293 cells are transfected with linearized plasmid pCMV-FIX-neo and selected in medium containing 500 μg/ml G418 (Invitrogen). Cell clones are isolated by limited dilution cloning techniques either manually or using a flow cytometric cell sorting technique.

FIX secretion into cell culture supernatants is detected by exchanging the growth medium for serum-free medium supplemented with 10 μg/ml vitamin K1 (Sigma). Supernatants are collected and FIX concentrations are determined by ELISA and clotting assay (activated partial thromboplastine time, APTT). For the calculation of specific secretion rates, cell numbers are counted using a CASY cell counter (Schärfe Systems, Reutlingen, Germany).

For transient co-expression experiments, the non-linearized plasmid pCMV-VKORC1-EDHPro (deposited at Budapest Treaty depository Deutsche Sammlung Von Mikroorganismen and Zellkulturen GmbH (DSMZ), 38124 Braunschweig, Germany under Deposit No. DSM 21249 on Mar. 5, 2008) is transfected using Lipofectamine 2000 reagent (Invitrogen). The same vector without rVKORC1 cDNA is used as negative control.

Analytical Methods

ELISAs are performed using a polyclonal rabbit anti-human FIX (Accurate Chemical, Westbury, N.Y.) in a 1:40000 dilution as primary antibody, and a polyclonal goat anti-human FIX horseradish-peroxidase conjugate as detection antibody. As a standard, a human plasma-derived FIX (Enzyme Research Laboratories, S. Lafayette, Ind.) is used. APTT is determined using a STA Compact automated coagulometer (Diagnostica Stago, Asnieres, France) by diluting FIX-samples into FIX deficient plama. All reagents for clotting are purchased from Baxter, Vienna, Austria.

Results

Two stable rFIX-producing cell lines, one CHO- and one HEK293-derived, are subjected to transient transfections with the expression vector pCMV-VKORC1-EDHpro carrying a cDNA encoding human VKORC1. As controls, the empty vector pCMV-EDHpro and the stable rFIX-expressing cell line are used. After transient transfections, the cells are left overnight in serum-containing medium. The cells are washed with PBS and cultivated for 24 hours in serum-free medium, then the supernatants are harvested. rFIX expression and secretion into the medium is monitored by immunochemical and coagulation diagnosis methods measuring antigen level or clotting activity. To estimate effects on cellular productivity, the secretion rates are calculated on the basis of product concentration per cell number and 24 hours (FIG. 1 to FIG. 4).

HEK293 cells expressing rFIX shows a 2.7-fold mean increase of specific secretion rates and a 2.9-fold increase of rFIX-concentrations after rVKORC1 transfection in comparison to the empty vector control. These values are based on APTT measurements. ELISA values shows a 2.0-fold increase of concentrations, and a 1.8-fold increase of specific productivities.

For the CHO-derived rFIX-producer cell line, a 1.5-fold increase of ELISA-titers, and a 1.2-fold increase of ELISA-based specific secretion rates are observed. APTT-calculated secretion rates are 1.4-fold higher, and APTT-measured FIX concentrations 1.7-fold.

From these values it can be concluded that for both different cell types higher rFIX product concentrations in presence of rVKORC1 can be achieved, mainly because of a higher cell specific rFIX secretion rate. A reason for a higher secretion rate of rFIX molecules with complete γ-carboxylation could be a cellular quality control mechanism for this post-translational modification (Lin et al. (2004) Binding of the factor IX gamma-carboxyglutamic acid domain to the vitamin K-dependent gamma-glutamyl carboxylase active site induces an allosteric effect that may ensure processive carboxylation and regulate the release of carboxylated product. *J. Biol. Chem.*, 279, 6560-6566). Higher increases of APTT values than ELISA values in case of both cell lines indicate also a better FIX-clotting activity.

Stronger effects of rVKORC1 on rFIX co-expression in HEK293-derived cells than in CHO cells can be explained by a higher cellular rFIX-productivity. Before transient VKORC1 transfections, the 293-derived clone has a 3.5-fold higher productivity than the CHO-clone in respect of APTT values, but a 5-fold higher productivity regarding ELISA values. This indicates a lower post-translational processing degree in the 293-derived cells because of a higher productivity. Therefore, a higher yield of active rFIX isoform when restoring γ-carboxylation capacity by rVKORC1 co-expression is found in this cell line.

Example 2

Transient Co-Expression of Recombinant Human VKORC1 in CHO- and HEK293-Derived Mammalian Cell Lines Stably Producing Recombinant Human Coagulation Factor VII (rFVII)

Any influence of rVKORC1 on the activity and/or secretion rate of rFVII can be studied by transient co-expression in human recombinant coagulation factor VII (rFVII) producing cells. Thus, a major part of the rFVII producing cell population also co-expresses VKORC1 for a short period of time. During this period, the secreted rFVII can be sampled, characterized and compared to the rFVII secreted by the same cell lines transfected in parallel with an empty vector control.

The stable expression of rFVII in mammalian cells can be achieved by transfecting plasmid vectors containing the human rFVII cDNA and selection resistance genes and subsequent producer clone selection. The same host cell lines as listed in Example 1 can be used for stable expression of rFVII. Genetic selection and gene amplification procedures, and the screening for producer clones have to be performed analogically.

After that, an expression vector carrying the human VKORC1 cDNA can be transfected transiently to achieve co-expression of recombinant VKORC1 (rVKORC1) in the same way as described in Example 1.

Materials and Methods
Expression Vectors

An expression vector comprising human rFVII genetic information can be constructed by isolating human FVII cDNA by PCR from an appropriate source like the vaccinia expression vector pselp/huFVII (Himly et al., (1998) *Prot. Expr. Purif.* 14, 317-326) as template. The PCR-product can be inserted via restriction sites into a mammalian expression vector offering a strong viral promoter as from cytomegalovirus (CMV) and an additional antibiotic selection marker like the neomycin or hygromycin resistance gene, for Example pcDNA3.1/hyg+ or pcDNA3.1/neo+ (Invitrogen, Carlsbad, Calif.).

For stable gene expression in the CHO-DHFR⁻ expression system an additional plasmid like pSV-DHFR as described in Example 1 can be used to enable selection of DHFR-containing cell clones and MTX-gene amplification.

The vector pCMV-VKORC1-EDHpro as described in Example 1 can be used for transient expression of rVKORC1.

Cell Culture and Transfections

The same cell lines and cultivation protocols can be used as described in Example 1. To generate stable transfectants, a calcium-phosphate co-precipitation method can be used. Plasmids have to be linearized by restriction enzyme digestion before transfections. A mammalian expression vector containing FVII cDNA can be used for stable transfection of CHO or HEK293 host cell lines. CHO DUKX DXB11 cells must be co-transfected with pSV-DHFR. If hygromycin B is used as selecting agent, its concentration should be 100 μg/mL in the medium to select HEK293-derived transfectants, and 250 μg/mL in case of CHO-transfectants. If neomycin resistance is used as selection marker, the concentrations of G418 should be adjusted as described in Example 1 for each cell type.

Transient transfection protocols include the use of Lipofectamine™ 2000 reagent as described in Example 1. To enable comparison of cells expressing rVKORC1 transiently with an adequate negative control, the vector pCMV-VKORC1-EDHpro and the same vector without the VKORC1 cDNA sequence should be transfected in parallel in several replications, preferably in 6-well plates. Cells derived from the same population are distributed at equal cell densities per well. At confluency, all transfections are performed simultaneously.

rFVII secretion into cell culture supernatants can be detected by exchanging the growth medium for serum-free medium supplemented with varying vitamin K1 concentrations ranging from 0.1 to 10 μg/mL. Supernatants can be collected after 24 hours and rFVII concentrations can be determined by appropriate methods as described below. For the calculation of specific rFVII secretion rates, cells should be counted for example by using a CASY cell counter (Schärfe Systems, Reutlingen, Germany), or the trypan-blue exclusion method.

Analytical Assays

To screen for rFVII producer clones, and to relate FVII-activities with antigen levels, the following assays are appropriate:

FVII activity can be measured in a clotting assay as prothrombin clotting time (PT) or in a chromogenic assay according to European Pharmacopeia 5 (5th edition 2.7.10.203 (2005)) as amount of clotting factor Xa (FXa) generation quantified by conversion of a chromogenic FXa substrate. FVII antigen levels can be determined by ELISA using appropriate antibody pairs, for example an affinity purified polyclonal sheep anti-human FVII antiserum (Affinity Biologicals, Ancaster, Canada) diluted 1:3000 for capture, and a polyclonal sheep anti-human FVII horseradish peroxidase conjugate (Cedarlane, Ontario, Canada; 1:2000 diluted) for detection, followed by addition of an appropriate chromogenic reagent for photometric detection.

For all assays, plasma-derived FVII preparations should be used as standard material, which are assayed against the international FVII standard 97/592. Relative specific clotting activities can be estimated by calculating ratios of measured antigen to activity values and comparing these internally or with values of plasma-derived or FVII preparations.

To estimate FVIIa levels as part of total secreted rFVII, the following assays can be used: The Staclot® assay (Diagnostica Stago, Asnieres, France) is adequate to measure a FVIIa prothrombin clotting time selectively (Morrissey et al. (1993) *Blood* 81, 734-44). FVIIa levels should be assayed against international FVIIa standard 89/688.

Results

Figure 5:
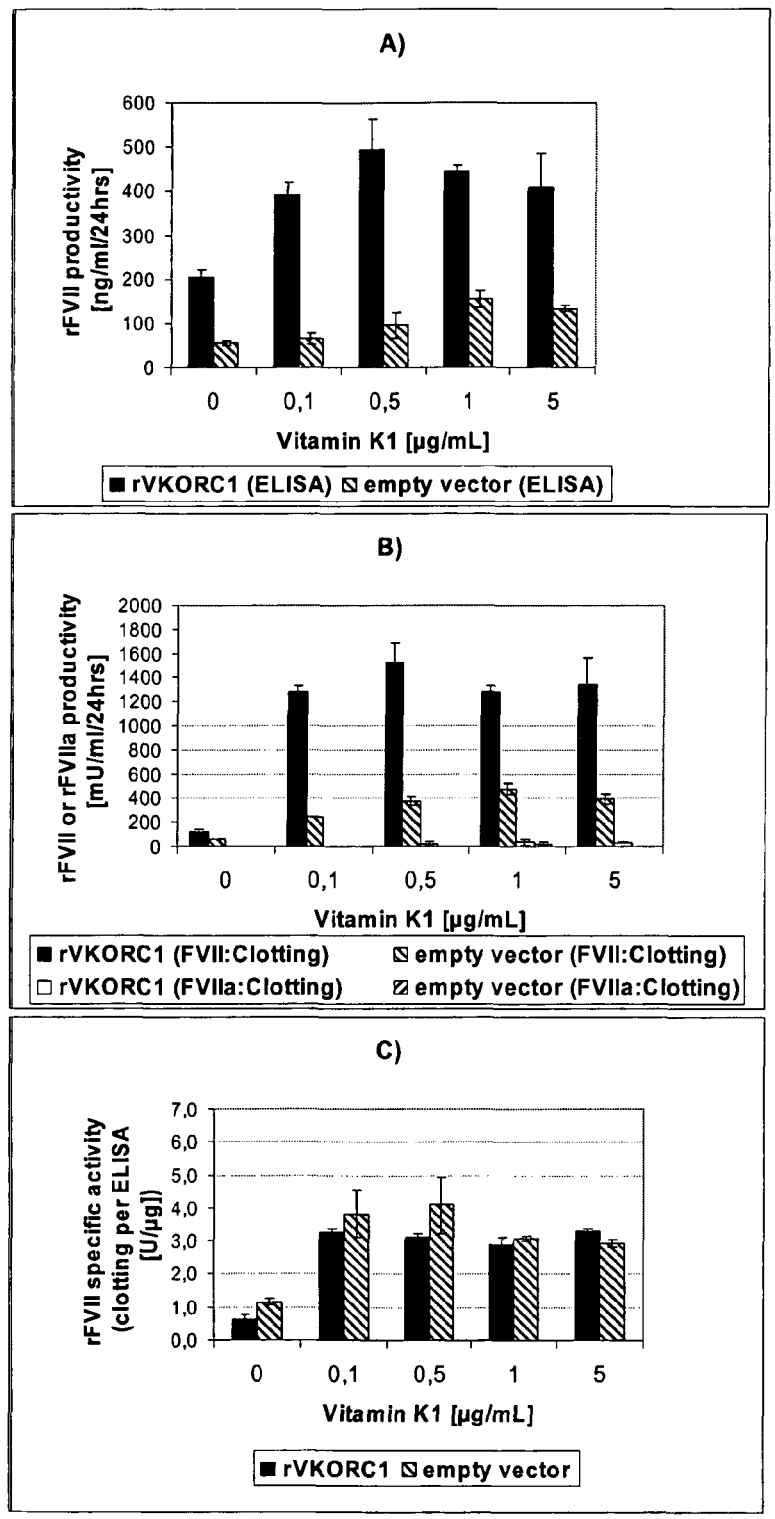
FIG. 5 shows transient expression of rVKORC1 in a CHO-derived cell line stably expressing rFVII. This cell line is transfected transiently with a vector encoding VKORC1 or the same vector without VKORC1 ("empty vector") as a control. Transfections are carried out in duplicate, and with subsequent use of 5 different vitamin K1 concentrations. Results of rFVII-productivity and -activity measurements in culture supernatants against vitamin K concentrations are shown.

A stable rFVII-producing CHO-derived cell line is subjected to transient transfections with a VKORC1 encoding expression vector pCMV-VKORC1-EDHpro. As a control, the empty vector pCMV-EDHpro without the VKORC1-encoding cDNA can be used. Cells are seeded into 6-well plates at cell concentrations of $1 \times 10^6$ cells per well. When confluency is reached, the transient transfection procedure is performed in duplicates. After overnight incubation, the cells are incubated in serum-free medium without any vitamin K1 to deplete the cells' internal vitamin K1 reservoirs from FBS-supplies. After 24 hours, the medium is exchanged for serum-free medium containing vitamin K1 at various concentrations ranging from 0 to 5 µg/mL. The supernatants are collected for further analysis. Productivities per 24 hours are determined from rFVII-antigen and activity concentration values as measured by ELISA and one-stage clotting assays. Specific FVII clotting activity is calculated as FVII-clotting-units per µg antigen. To estimate the degree of auto-activation of rFVIIa to rFVIIa, the Staclot® assay can be used. In FIGS. 5A, 5B and 5C, the results of these experiments are shown.

After transient transfection with both vector constructs, rFVII-expression levels are determined by ELISA (FIG. 5A) and FVII-clotting (FIG. 5B). There are no significant amounts of rFVIIa produced by the cell line, therefore rFVII-activity can be correlated to rFVII-productivity.

Without vitamin K1 in the medium, the cellular productivity and specific activity of the produced rFVII are significantly lower with and without rVKORC1 co-expression. In case of rVKORC1-co-expression, rFVII productivity recovers at 0.1 µg/mL to a 4-fold higher value as the control transfection with empty vector, as measured by both clotting and ELISA. rVKORC1-co-expression improves usage of vitamin K1 added to the cell culture medium regardless of the vitamin K1-concentration. In general, rFVII-productivity, determined by two different methods, is up to four times higher than the control at all vitamin K1 concentrations with rVKORC1 co-expression. Specific activity as expressed in clotting units per µg rFVII produced shows significant lower values only at 0 µg/mL vitamin K1, and does not show significant differences with and without rVKORC1.

Figure 6:
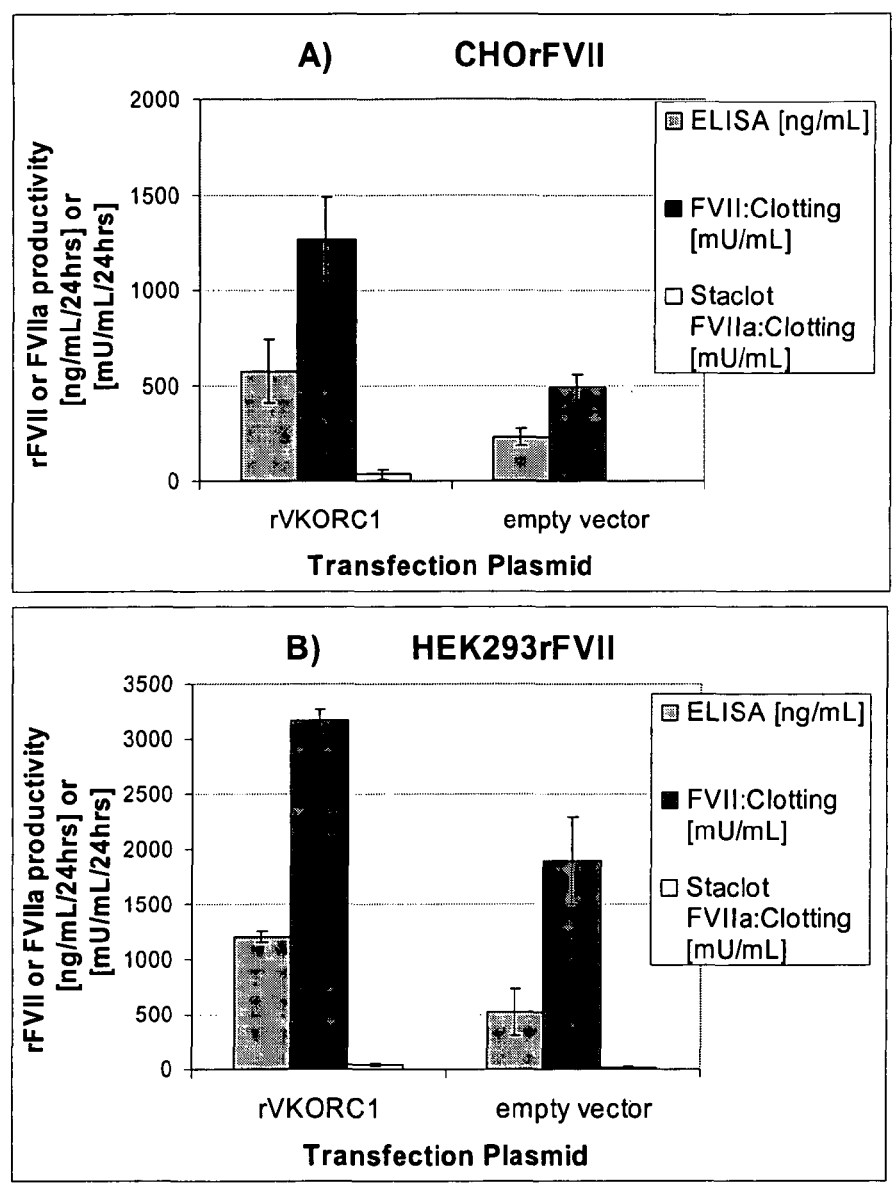
FIG. 6 shows transient expression of rVKORC1 in a CHO- and a HEK293-derived cell line stably expressing rFVII. These cell lines are transfected transiently with a vector encoding rVKORC1 or the same vector without rVKORC1 ("empty vector") as a control. Transfections are carried out in duplicate. Results of rFVII-productivity and -activity measurements based on ELISA and FVII- and FVIIa-clotting in culture supernatants are shown in a CHO-derived cell line (FIG. 6A) and a HEK293-derived cell line (FIG. 6B).

When comparing CHO-derived with HEK293-derived cell lines stably expressing rFVII after transient rVKORC1-co-expression in a similar experiment, significant higher productivities can be found as the control transfection in both cases (FIG. 6). In this experiment, 0.5 µg/mL vitamin K1 are used. For CHO-rFVII cells, a 2.5-fold higher rFVII expression level with rVKORC1 co-expression than the control can be found as determined by clotting and ELISA.

It can be concluded that γ-carboxylation is a rate limiting step for productivity of rFVII, when reduced vitamin K form required for this reaction is not available in sufficient amounts. A putative cellular control mechanism retains rFVII-molecules with incomplete γ-carboxylation inside the cell (Lin et al. (2004) *J. Biol. Chem.* 279, 6560-6566). Transient rVKORC1 co-expression improves rFVII productivity at a broad range of vitamin K1 concentrations by providing better supply of reduced vitamin K form ensuring complete γ-carboxylation.

These findings are again in accordance with previous works, where co-expression of γ-carboxylase led to a decrease of recombinant human factor IX productivity in mammalian cells (Hellgren et al. (2002) *Biochemistry* 41, 15045-15055). The only known function of VKORC1 within cellular metabolism to-date is the reduction of Vitamin K-2,3 epoxide to the hydroquinone form necessary for the γ-carboxylation reaction. Even if mammalian cell lines possess a well-functioning γ-carboxylation machinery per se, it can be concluded that rVKORC1 co-expression guarantees the desired rFVII protein quality of complete γ-carboxylation.

Example 3

Stable Bicistronic Co-Expression of rVKORC1 and rFVII in CHO-Derived Cell Lines after Non-Viral Gene Transfection To make use of any effect of rVKORC1 co-expression on γ-carboxylation within the scope of generating stable mammalian cell lines for rFVII production, a bicistronic expression system can be used. With such a system, the simultaneous expression of two proteins in eukaryotic cells after delivery of a single expression vector can be achieved. Moreover, the two proteins are translated from the same mRNA molecule simultaneously. This is enabled by introduction of a viral genetic element termed internal ribosome entry sequence (IRES) between the cDNAs encoding the two transgenes into the expression vector construct (Mountford and Smith (1995) 11, 179-184). After transcription of the mRNA from the DNA vector construct, which has been integrated stably into the host cell chromosome, two ribosomes can bind to the processed mRNA leading to simultaneous elongation of both polypeptide chains.

A vector has to be constructed providing elements for mammalian expression, for example strong viral promoters, polyadenylation signals and resistance genes enabling clone selection. Both cDNAs encoding the desired proteins are cloned into the vector with an IRES sequence in-between.

To compare rFVII expression with bicistronic rFVII and rVKORC1 co-expression, a control expression vector derived from exactly the same host vector carrying rFVII cDNA only can be constructed. These two vectors can be transfected in parallel into the same host cell line, for example the CHO-DHFR⁻ cell line CHO DUXK DXB11. This cell line offers the opportunity to enhance protein expression levels by gene amplification. This can be achieved by co-transfection of a plasmid carrying the DHFR gene and by increasing levels of the drug MTX during sub-cultivation as described in Example 1. By comparing the co-expression vector with the monocistronic rFVII vector in this expression and co-amplification system, the effects of gene-amplification on rFVII expression levels and activities in presence or absence of rVKORC1 as a helper protein can be observed. The selection of rFVII producer clones and characterization of produced rFVII can be achieved as explained in Example 2. To avoid clone-specific bias when comparing the two expression systems, a large number of clones, which have been screened by the same methodology, should be characterized.

Materials and Methods

Expression Vectors

Plasmid vector constructs, which are derived from the same host vector as explained in Example 2, can be constructed by standard cloning techniques. The construction of the vector pCMV-rFVII can be accomplished as described in Example 2, the analogue vector pCMV-rFVII-IRES-VKORC1 can be constructed as follows: the human FVII cDNA can be amplified via PCR from the same source as used in Example 2. The IRES element can be isolated from the source vector pIRES2-EGFP (Clontech, Palo Alto, Calif.), and the VKORC1 cDNA can be cloned from the same source vector as described in Example 1 (pCEP4-VKORC1). All three elements can be cloned into the same hast vector as used for construction of pCMV-rFVII (see Example 2). In detail, the FVII cDNA PCR product with an added Kozak's sequence and EcoRI restriction sites can be cloned into an intermediate vector (e.g. pBluescript; Stratagene, LaJolla, Calif.) to enable cleavage via appropriate restriction sites. A HindIII/BamHI fragment of this intermediate vector containing FVII cDNA can be cloned into pcDNA3.1/Hyg+ (Invitrogen). This intermediate construct can be digested with BamHI and XhoI to enable insertion of a BamHI/BstXI fragment from pIRES2-EGFP (containing IRES) together with a PCR product with VKORC1 cDNA (obtained from template pCEP4-VKORC1) and BstXI and XhoI sites at 5' and 3' ends simultaneously in one ligation reaction to obtain pCMV-rFVII-IRES-VKORC1.

To enable gene expression and amplification in the CHO-DHFR$^-$ expression system, a second selection plasmid pSV-DHFR as described in Example 1 can be used.

Cell Culture and Transfections

The CHO-DHFR$^-$-host cell line and the same materials and transfection and cultivation protocols as described in Example 1 can be used for the generation and selection of desired rFVII producer clones. Gene amplification with MTX can be accomplished analogically.

Analytical Assays

To characterize clones and supernatants for rFVII or activity and concentration, and to determine cell-specific productivity, the same assays as described in Example 2 can be used. FVIIa activity has to be monitored analogically.

Northern Blots

This technique can be used to detect transcription of the introduced genes specifically at mRNA level, and to check for correct mRNA sizes. Total cellular RNA isolated and prepared from a cell population can be separated on an agarose gel and blotted onto a nylon membrane. The specific RNA sequences can be detected via hybridization of a DIG-labeled Probe and developed with an alkaline-phosphatase-labeled anti DIG antibody (Roche, Basel, Switzerland) after binding to the hybridized probe by chemoluminescence on x-ray film. The target mRNA-levels (rVKORC1 and rFVII) should be compared against a house-keeping gene (e.g. hamster glyceraldehyde-phosphate-dehydrogenase (GAPDH)).

Results

Stable cell clones derived from the CHO-DHFR$^-$-expression systems can be generated and assayed for rFVII productivity by ELISA and prothrombin-time (PT) clotting techniques. The expression plasmids pCMV-rFVII-IRES-VKORC1 or pCMV-rFVII can be co-transfected with the selection plasmid pSV-DHFR by calcium-phosphate co-precipitation technique, and clones can be obtained by exposition to selection medium lacking hypoxanthine, glycine and thymidine and to antibiotic selection. Single-cell derived clones are screened after limited dilution cloning and are subcultivated several times with increasing MTX concentrations to achieve gene-amplification. Clones are exposed to MTX concentrations of up to 320 nM with every subcloning step. From all subcloning rounds, a total of 133 clones derived from pCMV-rFVII transfections and 83 clones derived from transfections with the rVKORC1 co-expression construct are expanded and characterized in detail. For cell culture supernatants, rFVII concentrations can be determined by ELISA, rFVII and rFVIIa activities are measured by PT clotting assays in parallel. Only clones with less than 10% of rFVII activated to FVIIa are considered for characterization to avoid artificially high specific FVII-clotting values. The expression levels are calculated from ELISA concentration values as ng per $10^6$ cells per 24 hours. Specific FVII-clotting activity is calculated as clotting units per µg.

Figure 7:
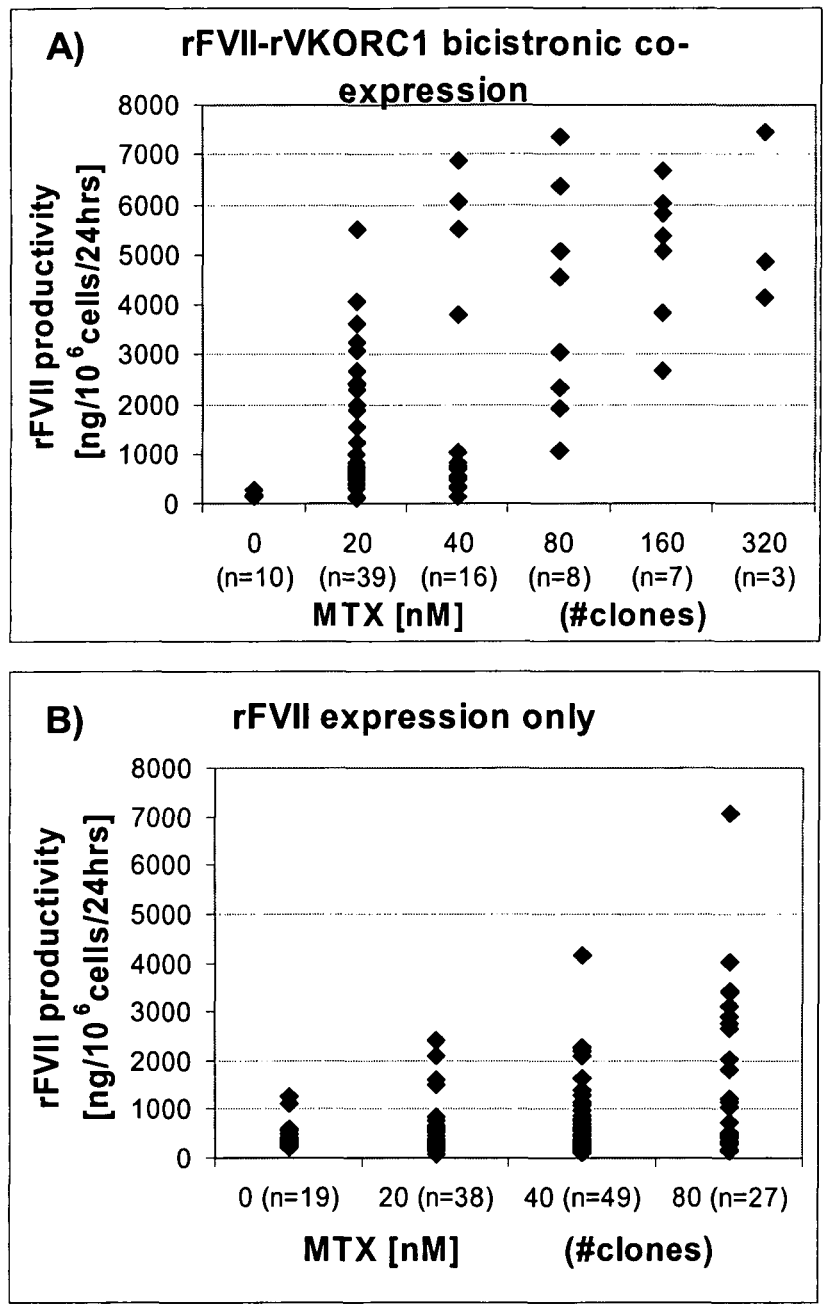
FIG. 7 shows stable bicistronic co-expression of rFVII and rVKORC in CHO-DHFR⁻ host cells. rFVII-Productivities of selected clones generated by gene co-amplification with increasing amounts of MTX. Two different human rFVII-encoding expression vectors have been co-transfected with a DHFR-encoding selection plasmid: 83 clones transfected with a vector construct causing bicistronic co-expression of rFVII and rVKORC1 (FIG. 7A) and 133 clones co-transfected with a rFVII-encoding vector (FIG. 7B).

In FIG. 7, specific productivity values on ELISA basis are plotted against MTX concentrations for rFVII only expressing clones (FIG. 7A), and rFVII-rVKORC1 co-expressing clones (FIG. 7B) respectively. In both lines a relationship between MTX levels and expression levels is visible. Initial clones at no MTX start at comparable, or even higher levels for the rFVII-only clones. Especially, when MTX is increased to low starting levels of 20 to 40 nM, a pattern of steeper concomitant increase of expression levels for rFVII-rVKORC1 co-expressing clones is clearly visible in FIG. 7A versus FIG. 7B. At 80 nM MTX, all rFVII-rVKORC1 co-expressing clones express 2 to 80 times more rFVII than initial clones, whereas for the rFVII-only clones, still some clones are found with expression levels similar to initial clones. From 20 nM upwards, better producer clones are found within rFVII-rVKORC1 than rFVII-only clones at all MTX levels. It can be seen, that the expression level of better rFVII-producer clones after gene amplification is two times higher with rVKORC1-co-expression especially at initial rounds of MTX increase.

Figure 8:
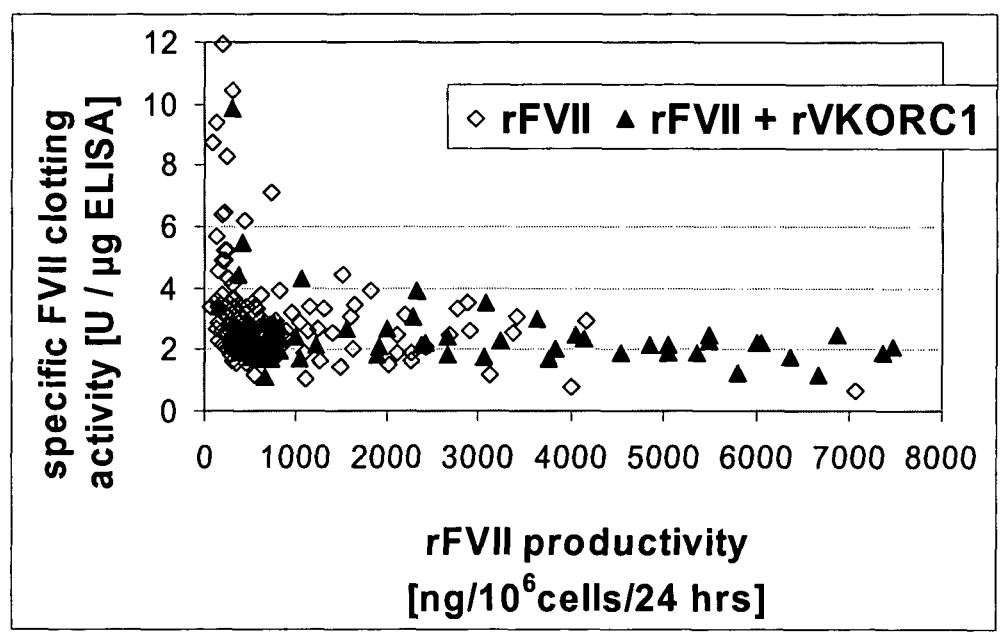
FIG. 8 shows productivity and specific activity values of CHO-derived clones producing rFVII with and without rVKORC1 bicistronic co-expression generated after stable transfection by subcloning and gene amplification. 133 clones without co-expression and 83 clones with rVKORC1 co-expression are compared in terms of rFVII productivity and specific clotting activity based on ELISA and FVII-clotting measurements of secreted rFVII.

Regarding specific FVII-clotting activity, the values calculated for all of these clones can be plotted against productivity to compare protein functionality. In FIG. 8, both lines are compared showing about equal activity values at similar productivity ranges with an overall decline at higher productivity for both. As rFVII-rVKORC1 co-producers with more than twofold higher productivity are found, the activity values at a range higher 4 µg per $10^6$ cells per day cannot be compared. Above this expression level in rFVII-rVKORC1 clones, a constant activity value of 2 U per µg similar to plasma-derived FVII (Moor et al. (1995) *Arterioscler. Thromb. Vasc. Biol.* 15, 655-664) can be maintained.

The functionality and functional genomic integration of the vector construct including the IRES element leading to transcription of a single bicistronic mRNA containing rFVII and rVKORC1 encoding sequences can be demonstrated by northern blotting technique, especially if there is no VKORC1-specific assay available.

Figure 3:
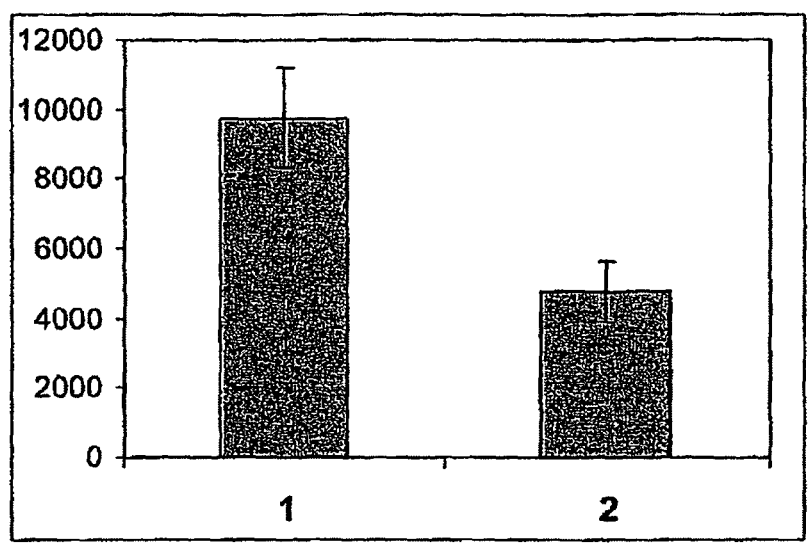
FIG. 3 shows the concentrations of rFIX in ng/ml (vertical axis) calculated on the basis of ELISA values (FIG. 3A) and the specific activities of rFIX calculated on the basis of clotting activity (APTT) values in mU/ml (vertical axis) (FIG. 3B) after transient transfections of a HEK293-derived rFIX producing cell line with rVKORC1 (1) or an empty vector (2). Serum-free cell culture supernatants were collected after 24 hours.
Figure 3:
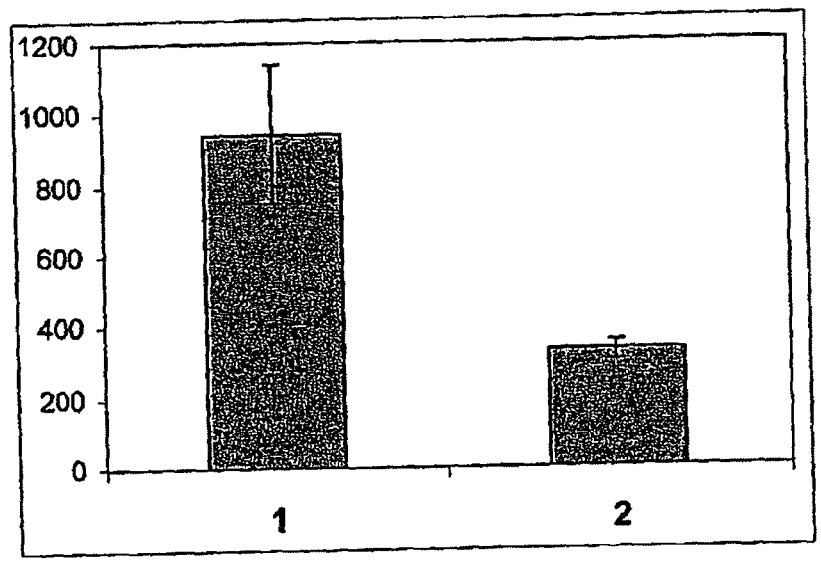
Figure 4:
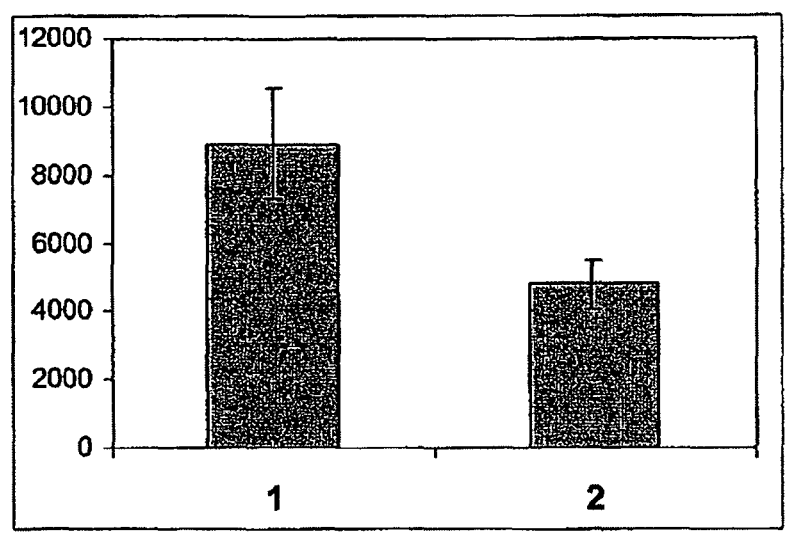
FIG. 4 shows the specific productivities of rFIX in ng rFIX/106 cells/day (vertical axis) calculated on the basis of ELISA values (FIG. 4A) and the specific activities of rFIX calculated on the basis of clotting activity (APTT) values in mU rFIX/106 cells/day (vertical axis) (FIG. 4B) after transient transfections of a HEK293-derived rFIX producing cell line with rVKORC1 (1) or an empty vector (2). Serum-free cell culture supernatants were collected after 24 hours.
Figure 4:
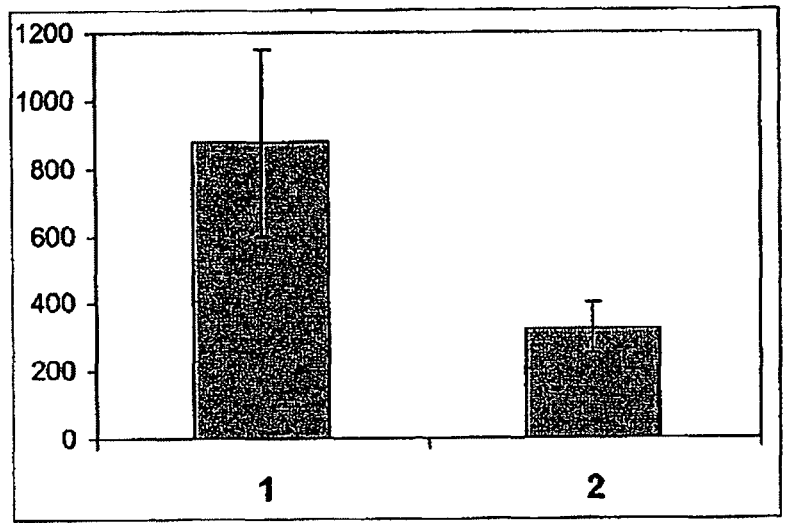

FIG. 3 shows an example of a northern blot, where total mRNA of CHO-derived transfectant or control cells has been isolated after cell lysis, and has been blotted on a nylon membrane after electrophoretic separation. The membrane has been hybridized three times subsequently with DIG-labeled DNA probes specific for human VKORC1, for human FVII, and for a reference gene, hamster GAPDH. Probes are detected with DIG-specific labeled antibodies. The samples are: non-transfected CHO-DHFR$^-$ cells, one CHO-derived clone expressing rFVII only, two clones, which have been transfected with rFVII- and rVKORC1-encoding vectors subsequently as described in Example 3, and three clones with bicistronic rFVII and rVKORC1 co-expression. mRNA transcripts with sizes of approximately 2.4 kb for the rFVII-IRES-rVKORC1 construct, of 1.4 kb for the rFVII construct, 0.5 kb for the rVKORC1 mRNA, and 1.0 kb for the GAPDH control mRNA, can be detected with all three probes. GAPDH can be found in all clones, whereas rVKORC1 and rFVII are present according to transfected plasmid vectors in the respective cell lines.

In summary, the stable bicistronic co-expression of rVKORC1 has an enhancing effect on productivity of rFVII in mammalian cells, especially when gene amplification is applied. The yield of rFVII-high-producer clones after gene transfer is higher with rVKORC1-co-expression. With half the number of clones screened, two-fold higher expression levels can be achieved at same MTX concentration levels. Protein activity can be maintained at high cellular protein secretion levels. Both effects can be explained by sufficient supply of reduced vitamin K form required for the γ-carboxylation reaction, which has to take place at a high turnover rate at high protein secretion levels to ensure timely release of the completely carboxylated protein.

Example 4

Stable Co-Expression of rFVII and rVKORC1 After Two Subsequent Non-Viral Transfections in CHO or HEK293 Mammalian Cells To verify rVKORC1 effects as helper protein on rFVII recombinant expression in mammalian cell culture, another approach can be used to achieve co-expression of rVKORC1 together with rFVII. A strategy to select for clones showing stable rFVII and rVKORC1 co-expression after a second transfection can be employed. A clone, which has been selected for rFVII expression after stable transfection, can be transfected a second time with another plasmid vector encoding human VKORC1. A second resistance marker can be introduced to ensure a selection step by resistance to another antibiotic. As an appropriate control, the same vector without VKORC1 cDNA can be transfected in parallel into the same cell population. From these transfections, stable clones can be isolated after simultaneous selection with two antibiotics within a cloning step and characterized as described in Examples 2 and 3. A comparison of these newly isolated clones should enable conclusions of rVKORC1 co-expression effects on rFVII productivity and activity.

Materials and Methods
Expression Vectors

To generate clones producing rFVII, the same expression vectors and source of rFVII cDNA as listed in Example 2 can be used. For the CHO-DHFR$^-$ system, an additional selection plasmid pSV-DHFR can be used.

To achieve rVKORC1 co-expression after a second transfection, a vector encoding human VKORC1 and a different antibiotic selection marker as used for the first transfection can be taken. This vector can be constructed by insertion of a PCR product generated from the same template as described in Example 1 into a pcDNA3.1 based vector (Invitrogen). In that case, the same pcDNA3.1 vector without insert should be taken for the second control transfection. Alternatively, the vector pCMV-VKORC1-EDHpro as described in Example 1 can be taken as expression vector for the same transfection. As control plasmid, the empty vector pCMV-EDHpro (see Example 1) can be used.

Cell Culture and Transfections

The same cell lines as used in Example 1, CHO and HEK293, can be used to generate stable cell lines producing rFVII. All cell culture media, transfection and cultivation protocols can be used accordingly. To achieve stable co-expression of rVKORC1 in these cell lines, a second transfection using calcium-phosphate co-precipitation can be used. Another cloning step using an additional antibiotic selection drug is necessary to obtain clones with rFVII and rVKORC1 co-expression.

Analytical Assays

The same assays for concentration and activity measurements as described in Examples 2 and 3 can be used to verify rFVII expression. rVKORC1 transcription at mRNA level can be shown by northern blot technique as described in Example 3.

Results

To demonstrate an effect of the rVKORC1 helper protein on the expression of rFVII, an approach of two subsequent transfections and cloning rounds can be employed. In the first round, cell clones expressing rFVII can be isolated by appropriate screening techniques after stable transfection and antibiotic selection. One of these clones can be expanded and used for a second transfection with a human VKORC1-encoding plasmid or an empty control plasmid. Another selection marker can be introduced. Again, clones can be screened for rFVII expression by appropriate techniques, after addition of the second antibiotic selection drug to the medium, thus ensuring depletion of non-transfected cells. Clones originating from rVKORC1- or control transfections can be compared in terms of rFVII productivity or activity. The empty control vector ensures comparison of clones being exposed to the same cultivation conditions with influence on rFVII expression, especially double-antibiotic selection.

Figure 9:
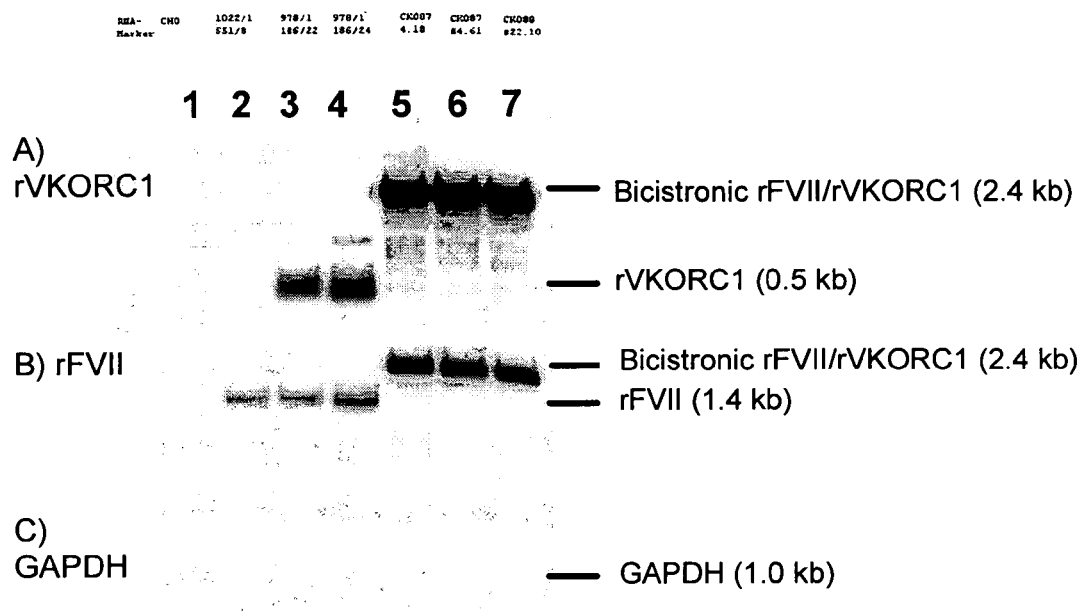
FIG. 9 shows northern blot analysis of gene expression at mRNA level isolated from CHO-derived cell lines. Lane 1: CHO-DHFR⁻ non-transfected cell line; Lane 2: rFVII clone; Lanes 3 and 4: two clones having been subsequently transfected with rFVII- and rVKORC1-encoding plasmid vectors as described in Example 4; Lanes 5 to 7: clones having been transfected with a single vector encoding a bicictronic mRNA with rFVII and rVKORC1 sequences coupled via IRES as described in Example 3 below. Panels A, B and C show the same blot developed after hybridization with three different probes: a probe for human VKORC1 (FIG. 9A); a probe for human FVII (FIG. 9B); and a probe for hamster GAPDH (FIG. 9C). Designations and sizes of identified mRNAs are given.

Typically, from all clones derived from successfully transfected cells, a small number of clones is selected according to their rFVII productivity and expanded for further characterization. This characterization includes determination of secreted rFVII concentrations by antigen ELISA technique and by measurement of rFVII and rFVIIa clotting activities. The co-expression of rVKORC1 and rFVII can be verified at mRNA level by northern blot technique as shown for two CHO-derived clones in FIG. 9, lanes 3 and 4.

Figure 10:
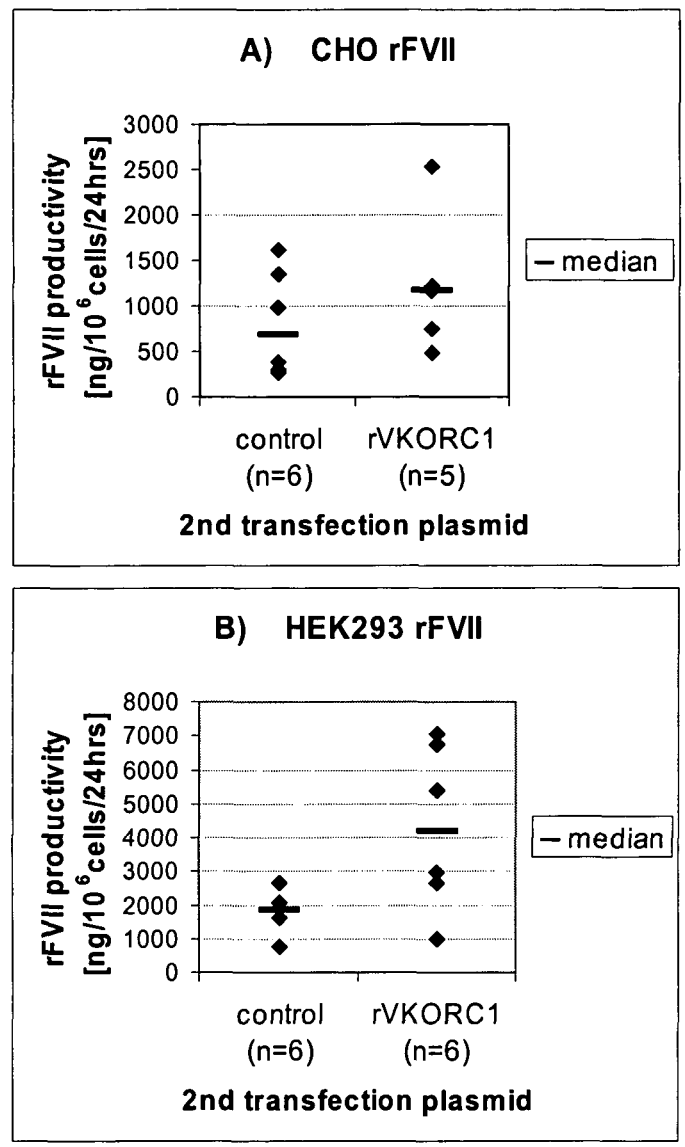
FIG. 10 shows rFVII expression levels of stably transfected CHO- and HEK293-derived cell clones isolated after a second transfection of rFVII-producing cell lines with a rVKORC1-encoding, or a control plasmid. The control is the empty host vector. Productivity values are based on ELISA measurements of secreted rFVII from CHO-derived cell clones (FIG. 10A) and HEK293-derived cell clones (FIG. 10B).

In FIG. 10, specific productivity values based on ELISA titers in culture supernatants are shown for a range of selected clones originating from rVKORC1 second transfections or control transfections of a CHO-derived (FIG. 10A) and a HEK293-derived (FIG. 10B) rFVII-producing cell line. It can be seen for both cell types, that clones derived from the rVKORC1 transfection produce more rFVII than those originating from the control transfection. The median value of all productivities is approximately two times higher for rVKORC1 clones in both cases.

Figure 11:
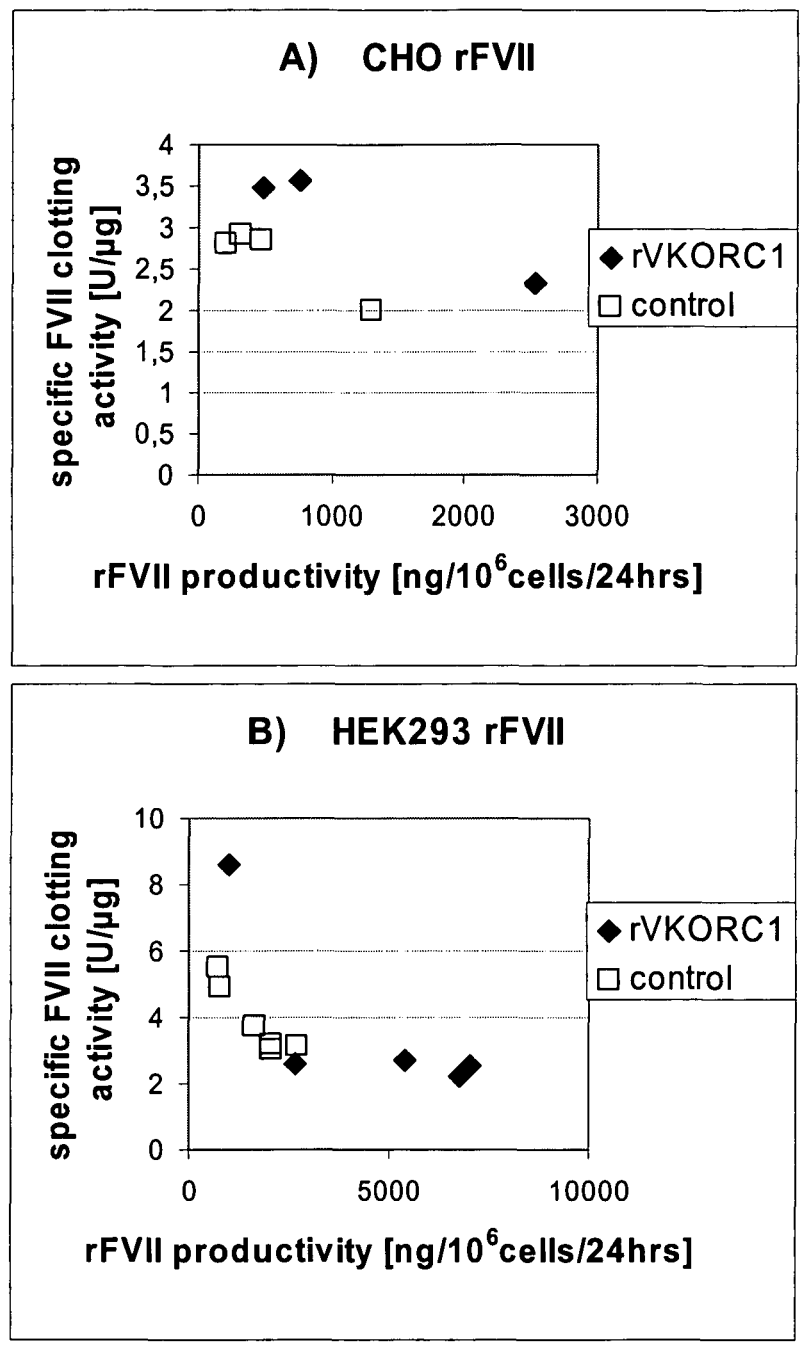
FIG. 11 shows rFVII expression levels compared against specific activity values of stably transfected CHO- and HEK293-derived cell clones isolated after a second transfection of rFVII-producing cell lines with a rVKORC1-encoding or a control plasmid. The control is the empty host vector. Productivity values are based on ELISA measurements of secreted rFVII. Specific activity values are calculated as FVII-clotting units per µg FVII as determined by ELISA.

In FIGS. 10A and 10B, the specific rFVII clotting activities given as FVII clotting units per microgram ELISA are shown for clones derived from both cell types after a second transfection. For specific activity calculations, clones with a high amount of rFVII activation to rFVIIa, which can be measured by FVIIa-specific clotting assay, should not be considered. A value of 10% FVIIa clotting units per FVII clotting units can be chosen to exclude clones producing a significant amount of rFVII activated to rFVIIa. Therefore fewer clones are shown in FIG. 11 than in FIG. 10.

Differences in specific FVII-clotting activity can be correlated rather with expression level than with rVKORC1 co-expression. However, in case of CHO-derived clones, clones with similar expression levels show higher activity in presence of rVKORC1 co-expression. Concerning productivity for both CHO- and HEK293-derived cell clones, it can be concluded that rVKORC1 co-expression leads to a two-fold mean improvement in comparison to a control. Moreover, it can be concluded, that rFVII activity is also affected by other factors influenced by the cell's metabolic protein secretion and modification capacity in addition to γ-carboxylation. Productivity and activity values are in agreement with results of rFVII/rVKORC1 co-expression experiments as described in Examples 2 and 3.

It is understood that the examples and embodiments described herein are for illustrative purposes only and that various modifications and changes in light thereof will be suggested to persons skilled in the art and are to be included within the purview of this application and are considered to be within the scope of the appended claims. All publications, Genbank Accession Nos., patents, and patent applications cited herein are hereby incorporated by referenced in their entirety for all purposes.

What is claimed is:

1. A recombinant mammalian cell comprising an exogenous recombinant nucleic acid encoding human vitamin K reductase complex subunit 1 (VKORC1) inserted into a plasmid and an exogenous recombinant nucleic add coding for a vitamin K dependent (VKD) procoagulant blood factor protein, wherein both the VKORC1 and the VKD protein are expressed in the mammalian cell, and wherein the mammalian cell does not overexpress γ-carboxylase;
   wherein the mammalian cell is selected from the group consisting of CHO cells, NSO cells, sp20 cells, Perc6 cells, SkHep cells, BHK cells, Hela cells, Vero cells, COS cells, and HEK293 cells, and
   wherein the procoagulant blood factor selected from the group consisting of Factor II, Factor VII, Factor IX and Factor X.

2. The recombinant mammalian cell of claim 1, wherein the VKD procoagulant blood factor protein is FVII or FIX.

3. The mammalian cell of claim 1, wherein the procoagulant blood factor is Factor IX, which is human Factor IX.

4. The mammalian cell of claim 1, wherein either the recombinant nucleic acid coding for the VKORC1 protein or the recombinant nucleic acid coding for the VKD protein or both the recombinant nucleic acids coding for the VKORC1 and the VKD proteins are expressed via an expression mode selected from the group consisting of induced, transient, and permanent expression.

5. A cell culture system comprising mammalian cells which have inserted therein an exogenous recombinant nucleic acid encoding a human vitamin K reductase complex subunit 1 (VKORC1) inserted into a plasmid and an exogenous recombinant nucleic acid coding for a vitamin K dependent (VKD) protein, wherein both the VKORC1 and the VKD protein encoded by the exogenous recombinant nucleic acids are expressed in said cells; wherein the cells do not overexpress γ-carboxylase; wherein the mammalian cells are selected from the group consisting of CHO cells, NSO cells, sp20 cells, Perc6 cells, SkHep cells, BHK cells, Hela cells, Vero cells, COS cells, and HEK293 cells; and
   wherein the VKD protein is a procoagulant blood factor selected from the group consisting of Factor II, Factor VII, Factor IX and Factor X.

6. The cell culture system of claim 5, wherein the procoagulant blood Factor protein is Factor IX, which is human Factor IX.

7. The cell culture system of claim 5, wherein the VKD procoagulant blood factor protein is FVII or FIX.

8. A method for improving the productivity of recombinant vitamin K dependent (VKD) protein expression in a mammalian cell comprising the steps of:
   (a) providing a mammalian cell in culture;
   (b) inserting an exogenous recombinant nucleic acid coding for a VKD procoagulant blood factor protein into the mammalian cell of step (a);
   (c) inserting an exogenous recombinant nucleic acid comprising the nucleotide sequence encoding a human vitamin K reductase complex subunit 1 (VKORC1) inserted into a plasmid into the mammalian cell of step (a); and
   (d) expressing the recombinant nucleic acids of steps (b) and (c); wherein the mammalian cell does not overexpress γ-carboxylase;
   wherein the mammalian cell is selected from the group consisting of CHO cells, NSO cells, sp20 cells, Perc6 cells, SkHep cells, BHK cells, Hela cells, Vero cells, COS cells, and HEK293 cells, and
   wherein the procoagulant blood factor selected from the group consisting of Factor II, Factor VII, Factor IX and Factor X.

9. The method of claim 8, wherein the VKD procoagulant blood factor protein is FVII or FIX.

10. A method for improving the productivity of recombinant vitamin K dependent (VKD) protein expression in a mammalian cell comprising the steps of:
    (a) providing a mammalian cell comprising an exogenous recombinant nucleic acid coding for a VKD procoagulant blood factor protein integrated into its genome;
    (b) inserting an exogenous recombinant nucleic acid comprising the nucleotide sequence of a recombinant nucleic acid encoding a human vitamin K reductase complex subunit 1 (VKORC1) inserted into a plasmid into the mammalian cell of step (a); and
    (c) expressing the recombinant nucleic acids of steps (a) and (b);
    wherein the mammalian cell does not overexpress γ-carboxylase;
    wherein the mammalian cell is selected from the group consisting of CHO cells, NSO cells, sp20 cells, Perc6 cells, SkHep cells, BHK cells, Hela cells, Vero cells, COS cells, and HEK293 cells; and
    wherein the procoagulant blood factor selected from the group consisting of Factor II, Factor VII, Factor IX and Factor X.

11. The method of claim 10, wherein the recombinant nucleic acid coding for the VKD procoagulant blood factor protein is stably expressed.

12. The method of claim 10, wherein the VKD procoagulant blood factor protein is FVII or FIX.

13. A method for improving the productivity of recombinant vitamin K dependent (VKD) procoagulant blood factor protein expression in a mammalian cell in culture, the method comprising the steps of:

(a) providing a mammalian cell comprising an exogenous recombinant nucleic acid comprising the nucleotide sequence encoding human vitamin K reductase complex subunit 1 (VKORC1) inserted into a plasmid integrated into its genome;
(b) inserting an exogenous recombinant nucleic acid coding for a VKD procoagulant blood factor protein into the mammalian cell of step (a); and
(c) expressing the recombinant nucleic acids of steps (a) and (b)
wherein the mammalian does not overexpress γ-carboxylase;
wherein the mammalian cell is selected from the group consisting of CHO cells, NSO cells, sp20 cells, Perc6 cells, SkHep cells, BHK cells, Hela cells, Vero cells, COS cells, and HEK293 cells, and
wherein the procoagulant blood factor selected from the group consisting of Factor II, Factor VII, Factor IX and Factor X.

14. The method of claim 13, wherein the recombinant nucleic acid coding for VKORC1 is stably expressed.

15. The method of claim 13, wherein the VKD procoagulant blood factor protein is FVII or FIX.

* * * * *

```
                             SEQUENCE LISTING

<160> NUMBER OF SEQ ID NOS: 1

<210> SEQ ID NO 1
<211> LENGTH: 6521
<212> TYPE: DNA
<213> ORGANISM: homo sapiens

<400> SEQUENCE: 1
gaattcgagc ttgcatgcct gcaggtcgtt acataactta cggtaaatgg cccgcctggc        60
tgaccgccca acgaccccg cccattgacg tcaataatga cgtatgttcc catagtaacg       120
ccaataggga ctttccattg acgtcaatgg gtggagtatt tacggtaaac tgcccacttg       180
gcagtacatc aagtgtatca tatgccaagt acgccccta ttgacgtcaa tgacggtaaa       240
tggcccgcct ggcattatgc ccagtacatg accttatggg actttcctac ttggcagtac       300
atctacgtat tagtcatcgc tattaccatg gtgatgcggt tttggcagta catcaatggg       360
cgtggatagc ggtttgactc acggggattt ccaagtctcc accccattga cgtcaatggg       420
agtttgtttt ggcaccaaaa tcaacgggac tttccaaaat gtcgtaacaa ctccgcccca       480
ttgacgcaaa tgggcggtag gcgtgtacgg tgggaggtct atataagcag agctcgttta       540
gtgaaccgtc agatcgcctg gagacgccat ccacgctgtt ttgacctcca tagaagacac       600
cgggaccgat ccagcctccg gactctagag gatccggtac tcgaatcgat tgagataatg       660
ggcagcacct gggggagccc tggctgggtg cggctcgctc tttgcctgac gggcttagtg       720
ctctcgctct acgcgctgca cgtgaaggcg gcgcgcgccc gggaccggga ttaccgcgcg       780
ctctgcgacg tgggcaccgc catcagctgt tcgcgcgtct tctcctccag gtggggcagg       840
ggtttcgggc tggtggagca tgtgctggga caggacagca tcctcaatca atccaacagc       900
atattcggtt gcatcttcta cacactacag ctattgttag gttgcctgcg gacacgctgg       960
gcctctgtcc tgatgctgct gagctccctg gtgtctctcg ctggttctgt ctacctggcc      1020
tggatcctgt tcttcgtgct ctatgatttc tgcattgttt gtatcaccac ctatgctatc      1080
aacgtgagcc tgatgtggct cagtttccgg aaggtccaag aacccaggg caaggctaag      1140 aggcactgag ccctgaattc tgcagatatc catcacactc tcgagcggt ccccccgggg      1200 gtaccatatt gccgtctttt ggcaatgtga gggcccggaa acctggccct gtcttcttga      1260
cgagcattcc tagggtctt tcccctctcg ccaaaggaat gcaaggtctg ttgaatgtcg      1320
tgaaggaagc agttcctctg gaagcttctt gaagacaaac aacgtctgta gcgaccctt      1380 gcaggcggcg gaacccccca cctggcgaca ggtgcctctg cggccaaaag ccacgtgtat      1440
```

```
aagatacacc tgcaaaggtg gcacaacccc agtgccacgt tgtgagttgg atagttgtgg    1500
aaagagtcaa atggctctcc tcaagcgtat tcaacaaggg gctgaaggat gcccagaagg    1560
taccccatcg tatgggatct gatctggggc ctcggtgcac atgctttaca tgtgtttagt    1620
cgaggttaaa aaaacgtcta ggccccccga accacgggga cgtggttttc ctttgaaaaa    1680
cacgataata ccatggttcg accattgaac tgcatcgtcg ccgtgtccca aaatatgggg    1740
attggcaaga acgagaccct accctggcct ccgctcagga acgagttcaa gtacttccaa    1800
agaatgacca caacctcttc agtggaaggt aaacagaatc tggtgattat gggtaggaaa    1860
acctggttct ccattcctga gaagaatcga ccttttaaagg acagaattaa tatagttctc    1920
agtagagaac tcaaagaacc accacgagga gctcattttc ttgccaaaag tttggatgat    1980
gccttaagac ttattgaaca accggaattg caagtaaag tagacatggt ttggatagtc    2040
ggaggcagtt ctgtttacca ggaagccatg aatcaaccag gccacctcag actctttgtg    2100
acaaggatca tgcaggaatt tgaaagtgac acgttttttcc cagaaattga tttgggaaa    2160 tataaacttc tcccagaata cccaggcgtc ctctctgagg tccaggagga aaaaggcatc    2220
aagtataagt ttgaagtcta tgagaagaaa ggtcgatttc cacccccgcc tccagtacgt    2280
aatcgacgga tcccgcctga actcaccgcg acgtctgtcg agaagtttct gatcgaaaag    2340
ttcgacagcg tctccgacct gatgcagctc tcggagggcg aagaatctcg tgctttcagc    2400
ttcgatgtag agggcgtgg atatgtcctg cgggtaaata gctgcgccga tggtttctac    2460
aaagatcgtt atgtttatcg gcactttgca tcggccgcgc tcccgattcc ggaagtgctt    2520
gacattgggg aattcagcga gagcctgacc tattgcatct cccgccgtgc acagggtgtc    2580
acgttgcaag acctgcctga aaccgaactg cccgctgttc tgcagccggt cgcggaggcc    2640
atggatgcga tcgctgcggc cgatcttagc cagacgagcg ggttcggccc attcggaccg    2700
caaggaatcg gtcaatacac tacatggcgt gatttcatat gcgcgattgc tgatccccat    2760
gtgtatcact ggcaaactgt gatggacgac accgtcagtg cgtccgtcgc gcaggctctc    2820
gatgagctga tgctttgggc cgaggactgc cccgaagtcc ggcacctcgt gcacgcggat    2880
ttcggctcca acaatgtcct gacggacaat ggccgcataa cagcggtcat tgactggagc    2940
gaggcgatgt cggggattc ccaatacgag gtcgccaaca tcttcttctg gaggccgtgg    3000
ttggcttgta tggagcagca gacgcgctac ttcgagcgga ggcatccgga gcttgcagga    3060
tcgccgcggc tccgggcgta tatgctccgc attggtcttg accaactcta tcagagcttg    3120
gttgacggca atttcgatga tgcagcttgg gcgcagggtc gatgcgacgc aatcgtccga    3180
tccggagccg ggactgtcgg gcgtacacaa atcgcccgca aagcgcggc cgtctggacc    3240 gatggctgtg tagaagtact cgccgatagt ggaaaccgac gccccagcac tcgtccgagg    3300
gcaaaggaat agagtagatg ccgaccgaac aagagctgat ttcgagaacg cctcagccag    3360
caactcgcgc gagcctagca aggcaaatgc gagagaacgg ccttacgctt ggtggcacag    3420
ttctcgtcca cagttcgcgg gatccccgcg gtaccaggcc cagatccact agttctaggg    3480
ccctatcgag gaactgaaaa accagaaagt taactggtaa gtttagtctt tttgtctttt    3540
atttcaggtc ccggatccgg tggtggtgca aatcaaagaa ctgctcctca gtggatgttg    3600
cctttacttc taggcctgta cggaagtgtt acttctgctc taaaagctgc ggaattgtac    3660
ccgcggccgc ggggatccag acatgataag atacattgat gagtttggac aaaccacaac    3720
tagaatgcag tgaaaaaaat gctttatttg tgaaatttgt gatgctattg ctttatttgt    3780
```

```
aaccattata agctgcaata acaagttaa caacaacaat tgcattcatt ttatgtttca    3840
ggttcagggg gaggtgtggg aggttttttc ggatcctcta gagtcgaagc ttggcgtaat   3900
catggtcata gctgtttcct gtgtgaaatt gttatccgct cacaattcca cacaacatac   3960
gagccggaag cataaagtgt aaagcctggg gtgcctaatg agtgagctaa ctcacattaa   4020
ttgcgttgcg ctcactgccc gctttccagt cgggaaacct gtcgtgccag ctgcattaat   4080
gaatcggcca acgcgcgggg agaggcggtt tgcgtattgg gcgctcttcc gcttcctcgc   4140
tcactgactc gctgcgctcg gtcgttcggc tgcggcgagc ggtatcagct cactcaaagg   4200
cggtaatacg gttatccaca gaatcagggg ataacgcagg aaagaacatg tgagcaaaag   4260
gccagcaaaa ggccaggaac cgtaaaaagg ccgcgttgct ggcgtttttc cataggctcc   4320
gcccccctga cgagcatcac aaaaatcgac gctcaagtca gaggtggcga acccgacag    4380
gactataaag ataccaggcg tttccccctg gaagctccct cgtgcgctct cctgttccga   4440
ccctgccgct taccggatac ctgtccgcct ttctcccttc gggaagcgtg gcgctttctc   4500
atagctcacg ctgtaggtat ctcagttcgg tgtaggtcgt tcgctccaag ctgggctgtg   4560
tgcacgaacc ccccgttcag cccgaccgct gcgccttatc cggtaactat cgtcttgagt   4620
ccaacccggt aagacacgac ttatcgccac tggcagcagc cactggtaac aggattagca   4680
gagcgaggta tgtaggcggt gctacagagt tcttgaagtg gtggcctaac tacggctaca   4740
ctagaagaac agtatttggt atctgcgctc tgctgaagcc agttaccttc ggaaaaagag   4800
ttggtagctc ttgatccggc aaacaaacca ccgctggtag cggtggtttt tttgtttgca   4860
agcagcagat tacgcgcaga aaaaaaggat ctcaagaaga tcctttgatc ttttctacgg   4920
ggtctgacgc tcagtggaac gaaaactcac gttaagggat tttggtcatg agattatcaa   4980
aaaggatctt cacctagatc cttttaaatt aaaaatgaag ttttaaatca atctaaagta   5040
tatatgagta aacttggtct gacagttacc aatgcttaat cagtgaggca cctatctcag   5100
cgatctgtct atttcgttca tccatagttg cctgactccc cgtcgtgtag ataactacga   5160
tacgggaggg cttaccatct ggccccagtg ctgcaatgat accgcgagac ccacgctcac   5220
cggctccaga tttatcagca ataaaccagc cagccggaag ggccgagcgc agaagtggtc   5280
ctgcaacttt atccgcctcc atccagtcta ttaattgttg ccgggaagct agagtaagta   5340
gttcgccagt taatagtttg cgcaacgttg ttgccattgc tacaggcatc gtggtgtcac   5400
gctcgtcgtt tggtatggct tcattcagct ccggttccca acgatcaagg cgagttacat   5460
gatcccccat gttgtgcaaa aaagcggtta gctccttcgg tcctccgatc gttgtcagaa   5520
gtaagttggc cgcagtgtta tcactcatgg ttatggcagc actgcataat tctcttactg   5580
tcatgccatc cgtaagatgc ttttctgtga ctggtgagta ctcaaccaag tcattctgag   5640
aatagtgtat gcggcgaccg agttgctctt gcccggcgtc aatacgggat aataccgcgc   5700
cacatagcag aactttaaaa gtgctcatca ttggaaaacg ttcttcgggg cgaaaactct   5760
caaggatctt accgctgttg agatccagtt cgatgtaacc cactcgtgca cccaactgat   5820
cttcagcatc ttttactttc accagcgttt ctgggtgagc aaaaacagga aggcaaaatg   5880
ccgcaaaaaa gggaataagg gcgacacgga aatgttgaat actcatactc ttcctttttc   5940
aatattattg aagcatttat cagggttatt gtctcatgag cggatacata tttgaatgta   6000
tttagaaaaa taaacaaata ggggttccgc gcacatttcc ccgaaaagtg ccacctgacg   6060
tctaagaaac cattattatc atgacattaa cctataaaaa taggcgtatc acgaggccct   6120
ttcgtctcgc gcgtttcggt gatgacggtg aaaacctctg acacatgcag ctcccggaga   6180
```

```
cggtcacagc ttgtctgtaa gcggatgccg ggagcagaca agcccgtcag ggcgcgtcag    6240
cgggtgttgg cgggtgtcgg ggctggctta actatgcggc atcagagcag attgtactga    6300
gagtgcacca tatgcggtgt gaaataccgc acagatgcgt aaggagaaaa taccgcatca    6360
ggcgccattc gccattcagg ctgcgcaact gttgggaagg gcgatcggtg cgggcctctt    6420
cgctattacg ccagctggcg aaaggggggat gtgctgcaag gcgattaagt tgggtaacgc    6480
cagggttttc ccagtcacga cgttgtaaaa cgacggccag t                        6521
```